United States Patent
Zielinski et al.

(10) Patent No.: US 9,707,399 B2
(45) Date of Patent: *Jul. 18, 2017

(54) CARDIAC RESYNCHRONIZATION THERAPY OPTIMIZATION BASED ON INTRACARDIAC IMPEDANCE AND HEART SOUNDS

(71) Applicant: Medtronic, Inc., Minneapolis, MN (US)

(72) Inventors: Todd M. Zielinski, Ham Lake, MN (US); Yong Kyun Cho, Excelsior, MN (US); Douglas Hettrick, Andover, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/204,464

(22) Filed: Jul. 7, 2016

(65) Prior Publication Data
US 2016/0317817 A1    Nov. 3, 2016

Related U.S. Application Data

(63) Continuation of application No. 14/158,533, filed on Jan. 17, 2014, now Pat. No. 9,387,330.

(51) Int. Cl.
  *A61N 1/00*    (2006.01)
  *A61N 1/365*   (2006.01)
  (Continued)

(52) U.S. Cl.
  CPC ........ *A61N 1/36585* (2013.01); *A61B 5/0535* (2013.01); *A61B 5/0538* (2013.01);
  (Continued)

(58) Field of Classification Search
  USPC .................................................. 607/18, 27
  See application file for complete search history.

(56) References Cited

U.S. PATENT DOCUMENTS

| 4,428,378 A | 1/1984 | Anderson et al. |
| 4,450,527 A | 5/1984 | Sramek |

(Continued)

FOREIGN PATENT DOCUMENTS

| CN | 1662278 A | 8/2005 |
| EP | 0 532 149 B1 | 6/1997 |

(Continued)

OTHER PUBLICATIONS

Hall et al., *Guyton and Hall Textbook of Medical Physiology, 12th Edition*, Saunders, Philadelphia, PA, 2011; pp. 265-268.

(Continued)

*Primary Examiner* — Nicole F Johnson
(74) *Attorney, Agent, or Firm* — Carol F. Barry

(57) ABSTRACT

Methods and/or devices used in delivering cardiac resynchronization therapy based on a plurality of device parameters (e.g., A-V delay, V-V delay, etc.) are optimized by setting a device parameter based on selection data. The selection data may be acquired by acquiring temporal fiducial points (e.g., heart sounds) associated with at least a part of a systolic portion of at least one cardiac cycle and/or temporal fiducial points associated with at least a part of a diastolic portion of the at least one cardiac cycle for each of a plurality of electrode vector configurations, and extracting measurements from the intracardiac impedance signal acquired for each of a plurality of electrode vector configurations based on the temporal fiducial points. The acquired selection data may be scored and used to optimize the device parameter.

19 Claims, 26 Drawing Sheets

(51) Int. Cl.
*A61N 1/368* (2006.01)
*A61B 5/053* (2006.01)

(52) U.S. Cl.
CPC ......... *A61N 1/3682* (2013.01); *A61N 1/3684* (2013.01); *A61N 1/3686* (2013.01); *A61N 1/36521* (2013.01)

(56) References Cited

U.S. PATENT DOCUMENTS

| | | | |
|---|---|---|---|
| 5,052,388 A | 10/1991 | Sivula et al. | |
| 5,454,377 A | 10/1995 | Dzwonczyk et al. | |
| 5,501,702 A | 3/1996 | Plicchi et al. | |
| 5,584,868 A | 12/1996 | Salo et al. | |
| 5,913,879 A | 6/1999 | Ferek-Petric et al. | |
| 5,999,854 A | 12/1999 | Deno et al. | |
| 6,223,082 B1 | 4/2001 | Bakels et al. | |
| 7,065,400 B2 | 6/2006 | Schechter | |
| 7,092,755 B2 | 8/2006 | Florio | |
| 7,139,609 B1 | 11/2006 | Min et al. | |
| 7,228,174 B2 | 6/2007 | Burnes et al. | |
| 7,366,567 B2 | 4/2008 | Zhu et al. | |
| 7,440,803 B2 | 10/2008 | Ni et al. | |
| 7,548,784 B2 | 6/2009 | Chinchoy | |
| 7,580,746 B2 | 8/2009 | Gilkerson et al. | |
| 7,614,308 B2 | 11/2009 | Berner et al. | |
| 7,650,181 B2 | 1/2010 | Freeman et al. | |
| 7,657,313 B2 | 2/2010 | Rom | |
| 7,684,863 B2 | 3/2010 | Parikh et al. | |
| 7,689,283 B1 | 3/2010 | Schecter | |
| 7,844,331 B2 | 11/2010 | Li et al. | |
| 7,848,810 B1 | 12/2010 | Nabutovsky et al. | |
| 7,869,871 B2 | 1/2011 | Salo et al. | |
| 7,914,452 B2 | 3/2011 | Hartley et al. | |
| 8,355,548 B2 | 1/2013 | Kovacs, Jr. et al. | |
| 8,639,328 B2 | 1/2014 | Hettrick et al. | |
| 9,199,086 B2 | 12/2015 | Zielinski et al. | |
| 9,387,330 B2 | 7/2016 | Zielinski et al. | |
| 9,415,231 B2 | 8/2016 | Hettrick et al. | |
| 2001/0047194 A1 | 11/2001 | Thompson et al. | |
| 2003/0204212 A1 | 10/2003 | Burnes et al. | |
| 2004/0087870 A1 | 5/2004 | Jarverud | |
| 2005/0165454 A1 | 7/2005 | Chinchoy | |
| 2005/0203429 A1 | 9/2005 | Judy | |
| 2006/0271121 A1 | 11/2006 | Ding et al. | |
| 2007/0055170 A1 | 3/2007 | Lippert et al. | |
| 2007/0142733 A1 | 6/2007 | Hatlestad et al. | |
| 2007/0191901 A1 | 8/2007 | Schecter | |
| 2007/0213778 A1 | 9/2007 | Burnes et al. | |
| 2008/0103530 A1 | 5/2008 | Vitense et al. | |
| 2008/0208274 A1 | 8/2008 | Zhu et al. | |
| 2008/0234594 A1 | 9/2008 | Brooks et al. | |
| 2008/0249375 A1 | 10/2008 | Obel | |
| 2008/0249583 A1 | 10/2008 | Salo et al. | |
| 2009/0043213 A1 | 2/2009 | Kovacs et al. | |
| 2009/0082823 A1 | 3/2009 | Shuros et al. | |
| 2009/0118783 A1 | 5/2009 | Patangay et al. | |
| 2009/0270933 A1 | 10/2009 | Hettrick et al. | |
| 2009/0270934 A1 | 10/2009 | Hettrick et al. | |
| 2009/0275854 A1 | 11/2009 | Zielinski et al. | |
| 2009/0275855 A1 | 11/2009 | Zielinski et al. | |
| 2009/0292334 A1 | 11/2009 | Rom | |
| 2009/0299203 A1 | 12/2009 | De Voir et al. | |
| 2010/0023078 A1 | 1/2010 | Dong et al. | |
| 2010/0030086 A1 | 2/2010 | Zielinski et al. | |
| 2010/0030087 A1 | 2/2010 | Hettrick et al. | |
| 2010/0030292 A1 | 2/2010 | Sarkar et al. | |
| 2010/0113962 A1 | 5/2010 | Hettrick et al. | |
| 2010/0121403 A1 * | 5/2010 | Schecter | A61B 5/0538 607/27 |
| 2010/0179608 A1 | 7/2010 | Limousin | |
| 2010/0185250 A1 | 7/2010 | Rom | |
| 2011/0087301 A1 | 4/2011 | Li et al. | |
| 2012/0109245 A1 | 5/2012 | Hettrick et al. | |
| 2012/0239104 A1 | 9/2012 | Rosenberg et al. | |
| 2013/0079839 A1 | 3/2013 | Lian et al. | |
| 2014/0142646 A1 | 5/2014 | Hettrick et al. | |
| 2015/0202436 A1 | 7/2015 | Zielinski et al. | |
| 2015/0202443 A1 | 7/2015 | Zielinski et al. | |

FOREIGN PATENT DOCUMENTS

| | | |
|---|---|---|
| EP | 1 453 572 B1 | 4/2008 |
| EP | 1 997 427 A1 | 12/2008 |
| WO | WO 2006/061822 A2 | 6/2006 |
| WO | WO 2006/061822 A3 | 4/2009 |
| WO | WO 2015/109071 A1 | 7/2015 |

OTHER PUBLICATIONS

International Search Report and Written Opinion for International Application No. PCT/US2011/034486, mailed Nov. 9, 2011; 10 pgs.
International Search Report and Written Opinion for International Application No. PCT/US2015/011561.
U.S. Appl. No. 15/219,595, filed Jul. 26, 2016, Hettrick et al.

* cited by examiner

FIG. 23A

| Impedance Vector 1 Cardiac Cycle 1 | |
|---|---|
| Measured Parameter | Value |
| $Z_{MAX}$ | |
| $Z_{MIN}$ | |
| AREA | |
| $t_{EJECTION}$ | |
| $SL_{EJECTION}$ | |
| $INT_{EJECTION}$ | |
| $t_{FILLING}$ | |
| $SL_{FILLING}$ | |
| $INT_{FILLING}$ | |
| $SL40\%_{EJECTION}$ | |
| $INT40\%_{EJECTION}$ | |
| $SL60\%_{FILLING}$ | |
| $INT60\%_{FILLING}$ | |
| $SL_{S1 \to S2}$ | |
| $INT_{S1 \to S2}$ | |
| $SL_{S2 \to S1}$ | |
| $INT_{S2 \to S1}$ | |

FIG. 23B

| Impedance Vector 1 Cardiac Cycles 1→3 | |
|---|---|
| MEAN ± STDV | Value |
| $Z_{MAX}$ | |
| $Z_{MIN}$ | |
| $Z_{MAX} - Z_{MIN}$ | |
| AREA | |
| $t_{EJECTION}$ | |
| $SL_{EJECTION}$ | |
| $INT_{EJECTION}$ | |
| $t_{FILLING}$ | |
| $SL_{FILLING}$ | |
| $INT_{FILLING}$ | |
| $SL40\%_{EJECTION}$ | |
| $INT40\%_{EJECTION}$ | |
| $SL60\%_{FILLING}$ | |
| $INT60\%_{FILLING}$ | |
| $SL_{S1 \to S2}$ | |
| $INT_{S1 \to S2}$ | |
| $SL_{S2 \to S1}$ | |
| $INT_{S2 \to S1}$ | |

FIG. 23C

| Impedance Vector 1 Ejection/Filling Ratios | |
|---|---|
| Ratios | Value |
| $t_{EJECTION} / t_{FILLING}$ | |
| $SL_{EJECTION} / SL_{FILLING}$ | |
| $INT_{EJECTION} / INT_{FILLING}$ | |
| $SL40\%_{EJECTION} / SL60\%_{FILLING}$ | |
| $INT40\%_{EJECTION} / INT60\%_{FILLING}$ | |
| $SL_{S1 \to S2} / SL_{S2 \to S1}$ | |
| $INT_{S1 \to S2} / INT_{S2 \to S1}$ | |

FIG. 24

Vector Optimization Table

| Value | PAV = % Intrinsic A-V Conduction Time | | | | | | | |
|---|---|---|---|---|---|---|---|---|
| | 90% | 80% | 70% | 60% | 50% | 40% | 30% | 20% |
| $Z_{MAX}$ | | | ✓ | | | | | |
| $Z_{MIN}$ | | | ✓ | | | | | |
| $Z_{MAX} - Z_{MIN}$ | | | ✓ | | | | | |
| AREA | | | | ✓ | | | | |
| $t_{EJECTION}$ | | | ✓ | | | | | |
| $SL_{EJECTION}$ | | | ✓ | | | | | |
| $INT_{EJECTION}$ | | | | ✓ | | | | |
| $t_{FILLING}$ | | | ✓ | | | | | |
| $SL_{FILLING}$ | | | | | | ✓ | | |
| $INT_{FILLING}$ | | | | ✓ | | | | |
| $SL40\%_{EJECTION}$ | | | | | | | | |
| $INT40\%_{EJECTION}$ | | | ✓ | | | | | |
| $SL60\%_{FILLING}$ | | | ✓ | | | | | |
| $INT60\%_{FILLING}$ | | | ✓ | | | | | |
| $SL_{S1 \to S2}$ | | | | ✓ | | | | |
| $INT_{S1 \to S2}$ | | | ✓ | | | | | |
| $SL_{S2 \to S1}$ | | | ✓ | | | | | |
| $INT_{S2 \to S1}$ | | | ✓ | | | | | |
| $t_{EJECTION} / t_{FILLING}$ | | | | ✓ | | | | |
| $SL_{EJECTION} / SL_{FILLING}$ | | | ✓ | | | | | |
| $INT_{EJECTION} / INT_{FILLING}$ | | | ✓ | | | | | |
| $SL40\%_{EJECTION} / SL60\%_{FILLING}$ | | | | ✓ | | | | |
| $INT40\%_{EJECTION} / INT60\%_{FILLING}$ | | | ✓ | | | | | |
| $SL_{S1 \to S2} / SL_{S2 \to S1}$ | | | | | | ✓ | | |
| $INT_{S1 \to S2} / INT_{S2 \to S1}$ | | | | ✓ | | | | |

Maximum Hits : 70%
Secondary Hits : 60%
Tertiary Hits: 50%

*OPTIMAL SETTING = 70%*

CARDIAC RESYNCHRONIZATION THERAPY OPTIMIZATION BASED ON INTRACARDIAC IMPEDANCE AND HEART SOUNDS

This application is a continuation of U.S. patent application Ser. No. 14/158,533, filed on Jan. 17, 2014 now issued as U.S. Pat. No. 9,387,330), which is incorporated herein by reference in its entirety.

The disclosure herein relates to methods for optimizing device parameters for delivering therapy to a patient's heart (e.g., paced AV and VV delay for cardiac resynchronization therapy (CRT)), for example, using intracardiac impedance signals, heart sounds, etc., and further to apparatus for performing such processes.

Cardiac resynchronization therapy has been clinically demonstrated to improve cardiac function in patients suffering from various cardiac conditions such as congestive heart failure. CRT may apply electrical stimulation, or pacing, to one or both ventricles and/or atria to improve cardiac chamber coordination, which in turn, may improve stroke volume, pumping efficiency, etc. The time interval between pacing the atria and the ventricles may be referred to as the AV delay and the time interval between pacing each of the ventricles may be referred to as the VV delay.

For example, CRT for heart failure (HF) patients has been shown to improve hemodynamic parameters, physical capacity, long-term quality of life, and reduce mortality and morbidity. For successful resynchronization to occur, the atrioventricular delay (AV delay) and interventricular delay (VV delay) may be optimized. Methods to optimize these parametric delays have been explored with various sensing mechanisms such as electrocardiography (ECG), electrograms (EGMs), arterial blood pressure and cutaneous impedance, and subsequently compared to the echocardiography (e.g., ultrasound) optimization method. However, echo optimization methods for CRT are often subjective and show high intra- and inter-individual variability.

CRT systems having automated selection of AV and VV delays without clinician intervention exist. For example, systems that automatically adjust AV and VV delays may be generally disclosed in U.S. Pat. No. 6,223,082 issued to Bakels, et al., U.S. Pat. No. 7,548,784 issued to Chinchoy, and U.S. Pat. No. 7,228,174 to Burnes, et al., each of which are incorporated herein by reference in their entirety.

Impedance sensors have been used in pacing systems for obtaining information associated with cardiac function. For example, U.S. Pat. No. 5,501,702 issued to Plicchi, et al. and U.S. App. Pub. No 2009/0275854 A1 to Zielinski et al., each of which are incorporated herein by reference in their entirety, discloses measuring impedance using various electrode combinations.

SUMMARY

The disclosure herein relates to methods to measure hemodynamic parameters with an implanted device using sensors, such as, for example, intracardiac impedance in combination with heart auscultations to assist in CRT optimization. For example, intracardiac impedance measurements made based on temporal fiducial points associated with the systolic and/or diastolic portions of the cardiac cycle (e.g., fiducial points acquired using heart sounds, impedance minimums and maximums, R-R intervals, etc.) may be used to optimize one or more device parameters (e.g., AV delay, VV delay, etc.).

One exemplary implantable medical device disclosed herein for use in delivering CRT to a patient's heart, wherein the cardiac resynchronization therapy is delivered based on a plurality of device parameters, may include a sensing module configured to monitor at least an intracardiac impedance between at least two electrodes to provide an intracardiac impedance signal, a therapy delivery module configured to deliver cardiac therapy to the patient's heart, and a control module coupled to the sensing module and the therapy delivery module and configured to: deliver cardiac resynchronization therapy to a patient at a plurality of options for at least one of the device parameters (e.g., a plurality of paced A-V delays, a plurality of paced V-V delays, a plurality of pacing sites, a plurality of pacing vectors, a plurality of locations for lead placement, etc.) and acquire selection data relating to each of the plurality of options for the at least one device parameter for at least one cardiac cycle. Acquiring the selection data at each of the plurality of options of the device parameter may include: acquiring temporal fiducial points associated with at least a part of a systolic portion of at least one cardiac cycle and temporal fiducial points associated with at least a part of a diastolic portion of the at least one cardiac cycle for each of a plurality of electrode vector configurations; acquiring, at each of the plurality of electrode vector configurations and about simultaneously with the acquired fiducial points, an intracardiac impedance signal; extracting measurements from the intracardiac impedance signal for each of the plurality of electrode vector configurations based on the temporal fiducial points and associated with the systolic portion of at least one cardiac cycle and associated with the diastolic portion of the at least one cardiac cycle; and determining selection data for each of the plurality of electrode vector configurations based on the extracted measurements. The control module may be further configured to use the acquired selection data relating to each of the plurality of options of the device parameter to set one option of the plurality of options for delivery of cardiac resynchronization therapy to the patient's heart.

One exemplary implantable medical device method for delivering cardiac resynchronization therapy to a patient's heart (e.g., wherein the cardiac resynchronization therapy is delivered based on a plurality of device parameters) may include delivering cardiac resynchronization therapy to a patient at a plurality of options for at least one of the device parameters; acquiring selection data relating to each of the plurality of options for the at least one device parameter for at least one cardiac cycle (e.g., wherein acquiring the selection data at each of the plurality of options of the device parameter may include acquiring temporal fiducial points associated with at least part of a systolic portion of at least one cardiac cycle and temporal fiducial points associated with at least part of a diastolic portion of the at least one cardiac cycle for each of a plurality of electrode vector configurations, acquiring, at each of the plurality of electrode vector configurations and about simultaneously with the acquired fiducial points of the systolic portion and the diastolic portion of the at least one cardiac cycle, an intracardiac impedance signal, extracting measurements from the intracardiac impedance signal for each of the plurality of electrode vector configurations based on the temporal fiducial points and associated with the systolic portion of at least one cardiac cycle and associated with the diastolic portion of the at least one cardiac cycle, and determining selection data for each of the plurality of electrode vector configurations based on the extracted measurements); and using the acquired selection data relating to each of the plurality of options of the device parameter to set one option of the plurality of options for delivery of cardiac resynchronization therapy to the patient.

Another exemplary implantable medical device for use in delivering therapy to a patient's heart may include a sensing module configured to monitor an intracardiac impedance between at least two electrodes to provide an intracardiac impedance signal and to monitor heart sounds of a patient (e.g., sensed heart sounds may be representative of mitral valve closure and aortic valve closure); a therapy delivery module configured to deliver cardiac resynchronization therapy to the patient's heart; and a control module coupled to the sensing module and the therapy delivery module and configured to acquire selection data relating to each of a plurality of paced conduction delays (e.g., at least one of a plurality of paced A-V delays and a plurality of paced V-V delays) for at least one cardiac cycle (e.g., wherein acquiring the selection data at each paced conduction delay may include sensing heart sounds defining temporal fiducial points associated with at least a diastolic portion of the at least one cardiac cycle for each of a plurality of electrode vector configurations, acquiring, at each of the plurality of electrode vector configurations and about simultaneously with the sensed heart sounds, an intracardiac impedance signal, extracting measurements from the intracardiac impedance signal for each of the plurality of electrode vector configurations based at least in part on the defined temporal fiducial points associated with the diastolic portion of the at least one cardiac cycle, and determining selection data for each of the plurality of electrode vector configurations based on the extracted measurements); and use the acquired selection data relating to each of the plurality of conduction delays to set one conduction delay of the plurality of conduction delays for delivery of cardiac resynchronization therapy to the patient.

Another exemplary implantable medical device method may include delivering cardiac resynchronization therapy to a patient at a plurality of paced conduction delays; acquiring selection data relating to each of the plurality of paced conduction delays for at least one cardiac cycle (e.g., wherein acquiring the selection data at each paced conduction delay may include sensing heart sounds defining temporal fiducial points associated with at least a diastolic portion of the at least one cardiac cycle for each of a plurality of electrode vector configurations, acquiring, at each of the plurality of electrode vector configurations and about simultaneously with the sensed heart sounds, an intracardiac impedance signal, extracting measurements from the intracardiac impedance signal for each of the plurality of electrode vector configurations based at least in part on the defined temporal fiducial points associated with the diastolic portion of the at least one cardiac cycle, and determining selection data for each of the plurality of electrode vector configurations based on the intracardiac impedance measurements); and using the acquired selection data relating to each of the plurality of conduction delays to set one conduction delay of the plurality of conduction delays for delivery of cardiac resynchronization therapy to the patient.

Another exemplary implantable medical device for use in delivering therapy to a patient's heart may include a sensing module configured to monitor an intracardiac impedance between at least two electrodes to provide an intracardiac impedance signal and to monitor heart sounds of a patient; a therapy delivery module configured to deliver cardiac therapy to the patient's heart; and a control module coupled to the sensing module and the therapy delivery module and configured to control delivery of cardiac resynchronization therapy to a patient at a plurality of paced conduction delays, acquire selection data relating to each of the plurality of paced conduction delays for at least one cardiac cycle (e.g., wherein acquiring selection data may include sensing heart sounds defining temporal fiducial points associated with a systolic portion of at least one cardiac cycle and defining temporal fiducial points associated with a diastolic portion of the at least one cardiac cycle for each of a plurality of electrode vector configurations, acquiring, at each of the plurality of electrode vector configurations and about simultaneously with the sensed heart sounds, an intracardiac impedance signal, extracting measurements from the intracardiac impedance signal for each of the plurality of electrode vector configurations based at least in part on the defined temporal fiducial points associated with the systolic portion of at least one cardiac cycle and the defined temporal fiducial points associated with the diastolic portion of the at least one cardiac cycle, and determining selection data for each of the plurality of electrode vector configurations based on the extracted measurements), and use the acquired selection data relating to each of the plurality of conduction delays to set one conduction delay of the plurality of conduction delays for delivery of cardiac resynchronization therapy to the patient.

Another exemplary implantable medical device method may include delivering cardiac resynchronization therapy to a patient at a plurality of paced conduction delays; acquiring selection data relating to each of the plurality of paced conduction delays for at least one cardiac cycle (e.g., wherein acquiring the selection data at each paced conduction delay may include sensing heart sounds defining temporal fiducial points associated with a systolic portion of at least one cardiac cycle and defining temporal fiducial points associated with a diastolic portion of the at least one cardiac cycle for each of a plurality of electrode vector configurations, acquiring, at each of the plurality of electrode vector configurations and about simultaneously with the sensed heart sounds, an intracardiac impedance signal, extracting measurements from the intracardiac impedance signal for each of the plurality of electrode vector configurations based at least in part on the defined temporal fiducial points associated with the systolic portion of at least one cardiac cycle and the defined temporal fiducial points associated with the diastolic portion of the at least one cardiac cycle, and determining selection data for each of the plurality of electrode vector configurations based on the intracardiac impedance measurements); and using the acquired selection data relating to each of the plurality of conduction delays to set one conduction delay of the plurality of conduction delays for delivery of cardiac resynchronization therapy to the patient.

Further, one or more embodiments of the devices or methods may include one or more of the following: the control module may be configured to acquire temporal fiducial points associated with the systolic portion or a defined segment within the systolic portion of at least one cardiac cycle and temporal fiducial points associated with the diastolic portion or a defined segment within the diastolic portion of the at least one cardiac cycle for each of a plurality of electrode vector configurations, the temporal fiducial points associated with the systolic portion of at least one cardiac cycle and the temporal fiducial points associated with the diastolic portion of the at least one cardiac cycle may include at least heart sounds representative of mitral valve closure (MVC) and aortic valve closure (AVC); the temporal fiducial points associated with the systolic portion of at least one cardiac cycle and the temporal fiducial points associated with the diastolic portion of the at least one cardiac cycle may include temporal fiducial points defined by at least intra-cardiac impedance signal minimum and maximum points (e.g., wherein acquiring selection data may include extracting measurements from the intracardiac impedance signal for each of the plurality of electrode vector configurations based at least in part on the temporal fiducial points defined by the intra-cardiac impedance signal minimum point and maximum point), the temporal fiducial points associated with the systolic portion of at least one cardiac cycle may include at least points associated with a first predetermined portion of an R-R interval and the temporal fiducial points associated with the diastolic portion of the at least one cardiac cycle comprise at least points associated with a second predetermined portion of the R-R interval (e.g., wherein acquiring selection data may include extracting measurements from the intracardiac impedance signal for each of the plurality of electrode vector configurations based at least in part on temporal fiducial points associated with a first predetermined portion of an R-R interval and based at least in part on temporal fiducial points associated with a second predetermined portion of an R-R interval), acquiring selection data relating to each of the plurality of options of the device parameter for at least one cardiac cycle may include acquiring selection data relating to each of the plurality of options of the device parameter for at least a plurality of cardiac cycles occurring at the end of a respiratory cycle, and extracting measurements from the intracardiac impedance signal may include extracting one or more parameters comprising minimums, maximums, slopes, integrals, differentials, and timing at which one or more of such parameters occurs relative to one or more fiducial points, the control module (e.g., to use the acquired selection data relating to each of the plurality of options of the device parameter to set one option of the plurality of options for delivery of cardiac resynchronization therapy to the patient) may be configured to provide a score for each of the plurality of options of the device parameter based on the acquired selection data for each vector configuration at each of the plurality of paced conduction delays and select an option of plurality of options of the device parameter based on the scores for the plurality of options of the device parameter for delivery of cardiac resynchronization therapy to the patient (e.g., a score may be provided for each of the plurality of options of the device parameter based on the acquired selection data for each vector configuration by giving one or more selection data parameters determined based on the intracardiac impedance measurements different weight in determining a score than other selection data parameters); the control module may be configured to use the acquired selection data to select an electrode vector configuration for delivery of cardiac resynchronization therapy to the patient; extracting measurements from the intracardiac impedance signal may include at least extracting a first derivative of the impedance and/or the timing of minimum impedance relative to a fiducial point; and the control module may be further configured to allow a user to set a window of allowed pacing conduction delays to which the conduction delay may be set. The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIGS. 23A-23C and 24 are tables for use in describing a scoring process for optimizing AV delay.

DETAILED DESCRIPTION OF EXEMPLARY EMBODIMENTS

Figure 1:
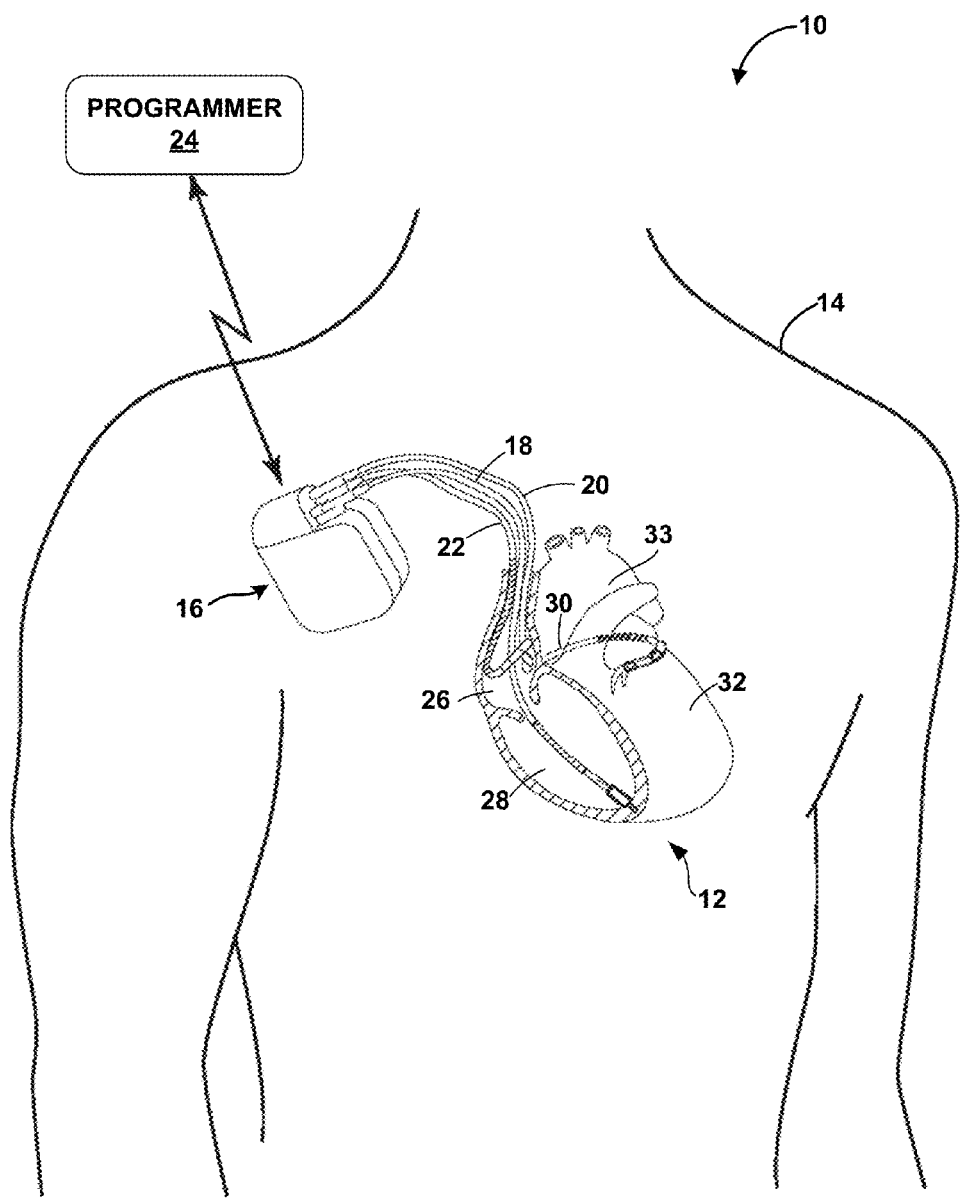
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-24. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

As described herein, various exemplary systems, apparatus, and methods may utilize electrodes configured to deliver therapy to tissue of a patient and/or sense one or more signals from the tissue of the patient (e.g., intracardiac impedance, etc.). For example, electrodes may be included as part of an implantable medical device (IMD) and located on one or more leads configured to be located proximate one or more portions of a patient's heart.

The exemplary methods and processes described herein may be utilized and implemented by one or more (e.g., two or more, a plurality, etc.) systems, apparatus, and devices that include and/or are coupled to at least one electrode. For example, the exemplary methods and processes may be used by an exemplary therapy system 10 described herein with reference to FIGS. 1-3. Although a therapy system 10 is described and depicted herein, it is to be understood that the exemplary methods and processes may be used by any system including computing apparatus capable of analyzing signals from one or more electrodes. The computing apparatus, for example, may be located in an external computer or programmer, may be located in an IMD, or may be located on a server attached to a network.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and/or a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to optimize one or more device parameters (e.g., paced AV delay, paced VV delay, etc.) using, for example, impedance signals sensed at electrodes of the systems (e.g., electrodes located on the leads 18, 20, 22) using the exemplary methods and processes described herein. In some examples, the IMD 16 provides pacing therapy (e.g., pacing pulses, CRT, etc.) to the heart 12 based on the electrical signals sensed within the heart 12. The IMD 16 may be operable to adjust one or more device parameters associated with the pacing therapy such as, e.g., paced AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes which can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning cardiac improvement information, longevity information (e.g., capture threshold information, impedance values, etc.) with respect to one or more electrical vectors, and/or provide sensed data (e.g., heart sound data, impedance signals, etc.). Additionally, the user may interact with the programmer 24 to select one or more optimal device parameters, e.g., for use in delivering therapy, such as AV delay and VV delay, electrode vector to be used for pacing, etc. Further, the user may interact with the programmer 24 to retrieve information concerning selection data associated with the IMD 16 and/or the pacing therapy delivered therewith. For instance, computing apparatus located in one or both of the IMD 16 and the programmer 24 may be configured to analyze or evaluate signals (e.g., impedance signals, heart sounds, R-R interval, etc. or data associated therewith) to identify one or more optimal device parameters (e.g., AV delay). The IMD 16 and the programmer 24 may communicate via wireless communication using any techniques known in the art. Examples of communication techniques may include, e.g., low frequency or radiofrequency (RF) telemetry, but other techniques are also contemplated. The IMD and programmer may be used to initialize the IMD with optimized device parameters as described herein or the IMD may carry out such optimization without the programmer (e.g., optimization may be provided at implant or after implant).

Figure 2A:
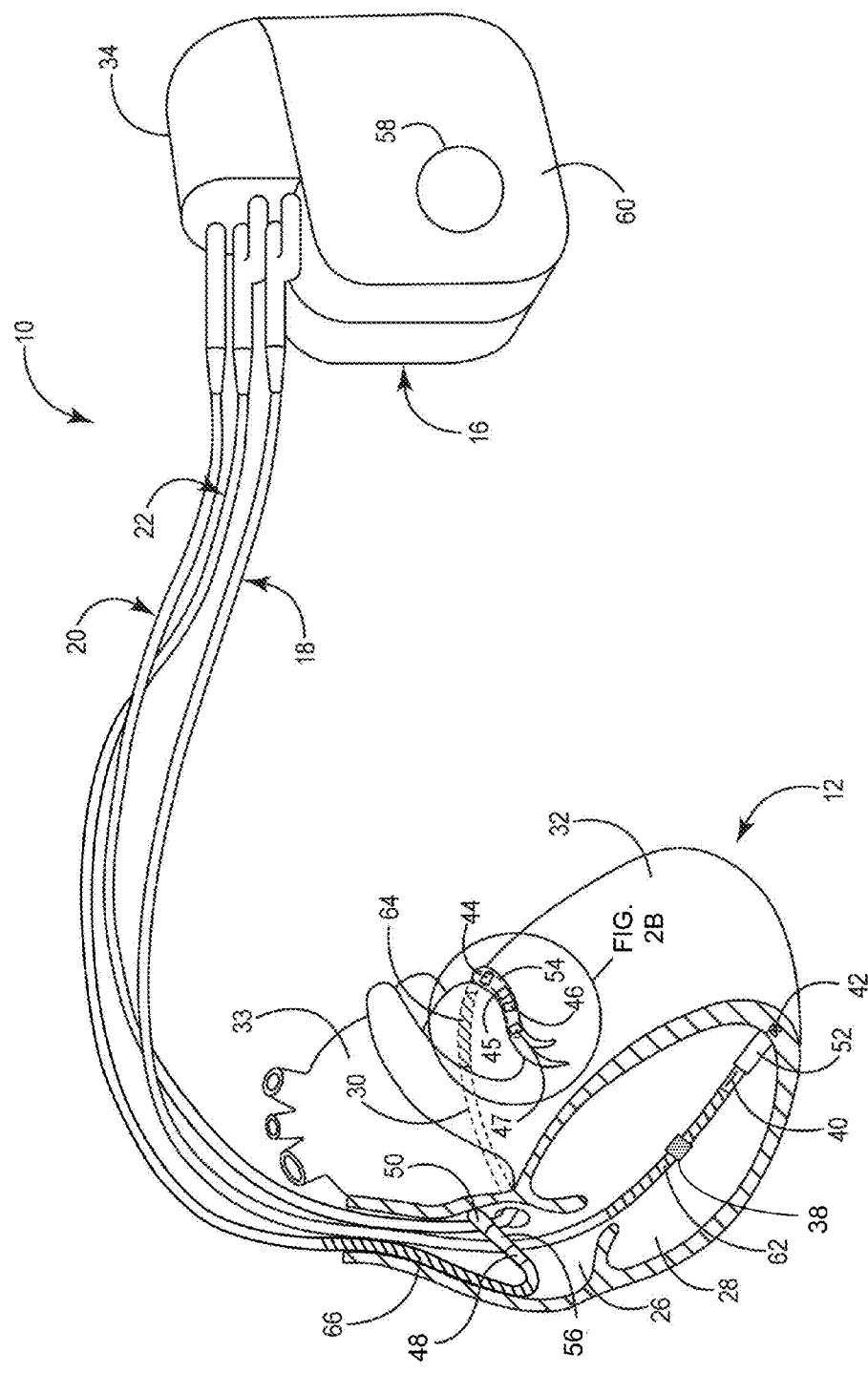
FIG. 2A is a diagram of the exemplary IMD of FIG. 1.

FIG. 2A is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 45, 46, 47 are located proximate to a distal end of the lead 20 and the bipolar electrodes 48, 50 are located proximate to a distal end of the lead 22.

The electrodes 40, 44, 45, 46, 47, 48 may take the form of ring electrodes mounted with respect to, and the electrodes 42, 50 may take the form of extendable helix tip electrodes mounted retractably within, the insulative electrode heads 52, 54, 56. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM), etc.) attendant to the depolarization and repolarization of the heart 12, sense intracardiac impedance, etc. The sensed electrical signals may be used to determine which of the electrodes 40, 42, 44, 45, 46, 47, 48, 50 are the most effective in improving cardiac function, may be used to optimize device parameters, acquire selection data as described herein, etc. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. In other words, any of electrodes 40, 42, 44, 45, 46, 47, 48, 50, 58 may be used in combination to form a sensing vector (e.g., a sensing vector that may be used to evaluate and/or analyze the pacing therapy, used to acquire selection data, acquire intracardiac impedance signal, etc.). It is generally understood by those skilled in the art that other electrodes can also be selected to define, or be used for, pacing and sensing vectors. Further, any of electrodes 40, 42, 44, 45, 46, 47, 48, 50, 58, which are not being used to deliver pacing therapy, may be used to sense electrical activity during pacing therapy.

As described in further detail with reference to FIGS. 3A-3B, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in acquiring intracardiac impedance waveforms, for acquiring signals for use in providing impedance measurements, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector).

Figure 2B:
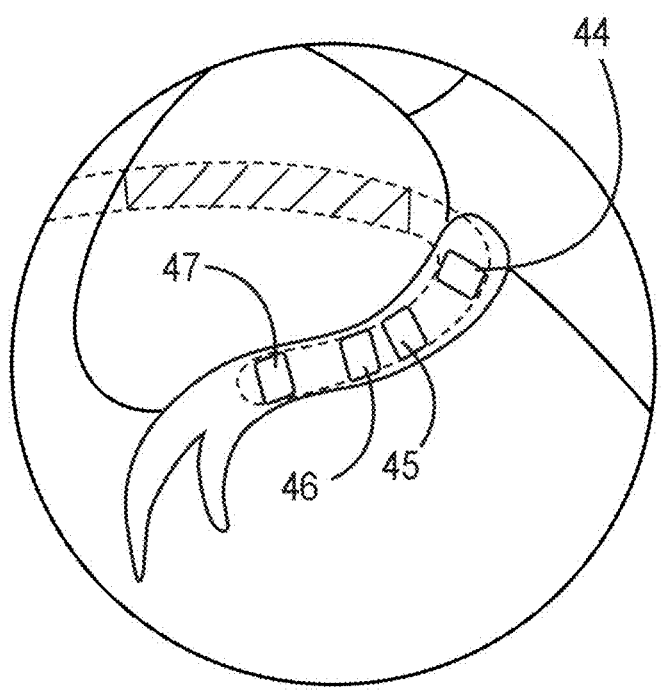
FIG. 2B is a diagram of an enlarged view of a distal end of the electrical lead disposed in the left ventricle of FIG. 2A.

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3A:
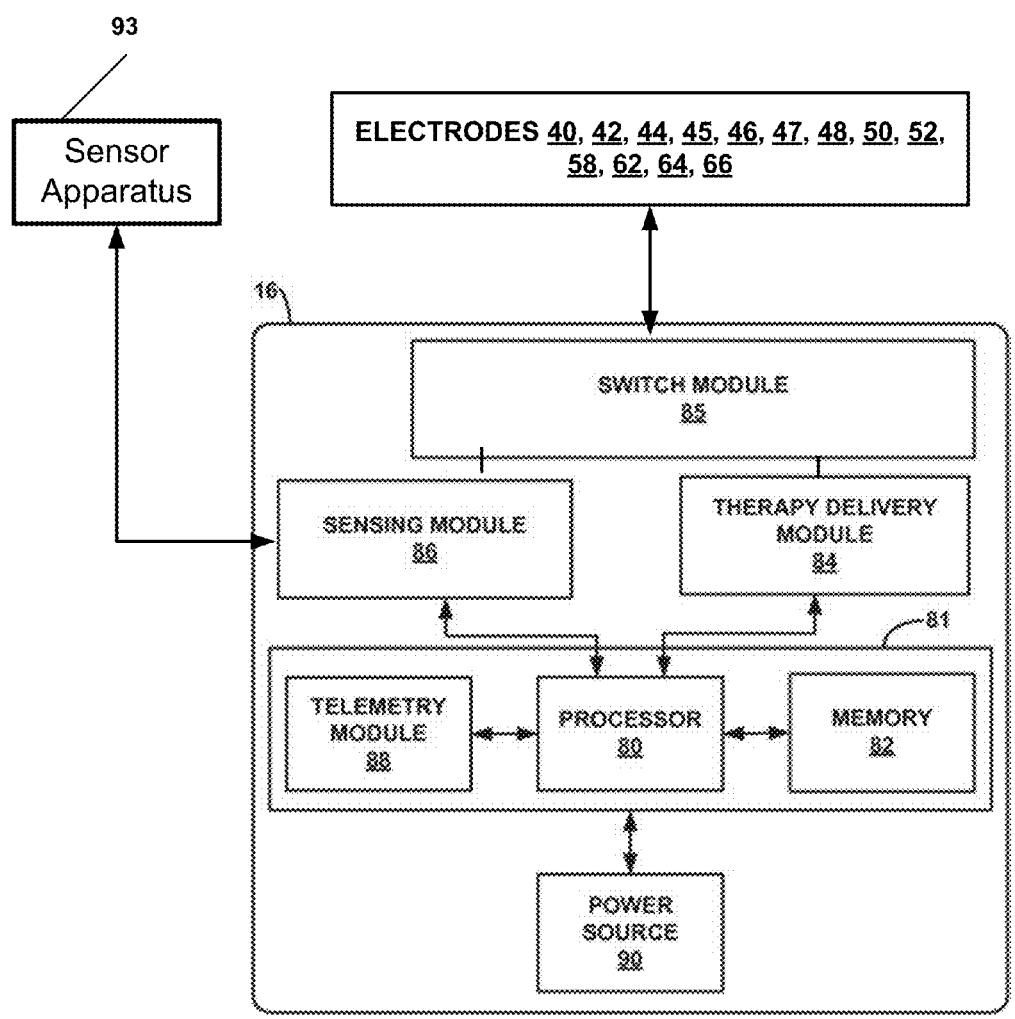
FIG. 3A is a block diagram of an exemplary IMD, e.g., the IMD of FIGS. 1-2.

FIG. 3A is a functional block diagram of one exemplary configuration of the IMD 16. As shown, the IMD 16 may include a control module 81, a therapy delivery module 84

(e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein (e.g., including capture management). Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine device parameters (e.g., paced AV delay, paced VV delay, an effective electrode vector configuration, etc.) using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV delay selection and/or adjustment programs as described herein, VV delay selection and/or adjustment programs as described herein, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or helical tip electrodes 42 and 50 of leads 18 and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing (e.g., select electrode vector configurations for pacing, select electrode vector configurations for sensing, etc.). The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to provide information for one or more functions, including those described herein for setting one or more device parameters (e.g., intializing and/or adjusting device parameters to provide optimization thereof, such as AV delay and VV delay, for example, by monitoring or measuring the signals for analysis by the control module 81, the programmer 24, etc.). Further, the ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vector configurations using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vector configurations using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness, etc. For example, the processor 80 may be configured to determine, or obtain, one or more features of one or more sensed morphological waveforms within one or more electrical vectors of the patient's heart and store the one or more features within the memory 82 for use in comparing features, values, etc. of the waveforms to set device parameters, etc.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

In one or more embodiments, one or more electrical vector configurations, for example, using any combination of the electrodes 40, 42, 44, 45, 46, 47, 48, 50, 58, 62, 64, 66 and/or any other electrodes may further be used to sense impedance (e.g., intracardiac impedance signals within the patient's heart 12). Impedance signals can be measured in a tissue segment (e.g., heart tissue segment) located in an electrode vector field between any two or more of the electrodes by measuring a voltage between two or more selected electrodes upon injecting a current between two or more selected electrodes; the impedance being determined, for example, based on the injected current and the measured voltage. The impedance may change due to a change in the characteristics of the tissue in the electrode vector field (e.g., degradation of the cellular wall due to disease), due to a change in the distance between electrodes (e.g., the change in distance between the left ventricle and the right ventricle), and/or due to a change in blood volume contained with the electrode vector field.

For example, the IMD 16 may measure an intracardiac impedance signal by injecting a current and measuring a voltage between electrodes of an electrode vector configuration (e.g., selected electrodes). For example, the IMD 16 may measure an impedance signal by injecting a current (e.g., a non-pacing threshold current) between electrode 42 and an electrode (not depicted) located in the right ventricle proximate the tricuspid valve and measuring a voltage between electrode 40 and the electrode (not depicted) located in the right ventricle proximate the tricuspid valve.

Still further, for example, the IMD 16 may measure an impedance signal by injecting a current between electrode 50 and electrode 42 and measuring a voltage between electrode 48 and electrode 40. One will recognize that other vector pair configurations may be used for stimulation and measurement. Impedance can be measured between any set of electrodes that encompass the tissue or cardiac chamber of interest. Thus, one can inject current and measure voltage to calculate the impedance on the same two electrodes (a bipolar configuration) or inject current and measure voltage on two separate pairs of electrodes (e.g., one pair for current injection and one pair for voltage sense), hence, a quadrapolar configuration. For a quadrapolar electrode configuration, the current injection and voltage sense electrodes should be in line with each other (or closely parallel to) and the voltage sense electrodes should be within the current sense field. For example, if one injected current between the SVC coil electrode and the RV tip electrode, voltage sense may be between the RVC coil electrode and RV ring electrode. The impedance vectors can be configured to encompass a particular anatomical area of interest, such as the atrium or ventricles.

The exemplary methods and/or devices described herein may monitor one or more electrode vector configurations. Further, multiple impedance vectors may be measured concurrently and/or periodically relative to another. In at least one embodiment, the exemplary methods and/or devices may use impedance waveforms to acquire selection data (e.g., to find applicable fiducial points, to allow extraction of measurements from such waveforms, etc.) for optimizing CRT.

As used herein, the term "impedance signal" is not limited to a raw impedance signal. It should be implied that raw impedance signals may be processed, normalized, and/or filtered (e.g., to remove artifacts, noise, static, EMI, and/or extraneous signals) to provide the impedance signal. Further, the term "impedance signal" may include various mathematical derivatives thereof including real and imaginary portions of the impedance signal, a conductance signal based on the impedance (i.e., the reciprocal or inverse of impedance), etc. In other words, the term "impedance signal" may be understood to include conductance signals, i.e. signals that are the reciprocal of the impedance signal.

Further, other sensor apparatus 93 may be coupled to sensing module 86 via any suitable interface (e.g., electrically coupled, coupled via amplifiers, analog to digital convertors, buffers, etc.) to monitor other heart related activity, such as acoustic data (e.g., heart sounds, including mitral valve closure and aortic valve closure, S1 and S2 as described herein, etc.). For example, in one or more embodiments, such sensor apparatus 93 may include any suitable transducer components (e.g., mounted within the implanted device, mounted on the can of the device, etc.) for sensing valve activity, such as a sonomicrometer, an accelerometer, a cardiomechanical sensor (CMES) employing embedded piezoelectric material on an implanted lead or alternate piezoelectric sensor. In other embodiments, heart valve events, such as mitral valve closure and aortic valve closure, may be detected using non-acoustic sensors, including, for example, sensors embedded in the myocardium or pressure Sensors implanted to detect chamber pressures, etc. Such detected valve events (e.g., heart sounds) may be used to provide information for one or more functions, including those described herein for setting one or more device parameters (e.g., intializing or adjusting device parameters to provide optimization thereof, such as AV delay and VV delay, for example, by monitoring or measuring the signals for analysis by the control module 81, the programmer 24, etc.).

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

In at least one embodiment, the control module 81 may transmit impedance signal data (e.g., produced by using various electrodes proximate the patient's heart 12) and/or any other data usable for setting device parameters as described herein using the telemetry module 88 to an external device, such as the programmer 24, such that a clinician and/or patient may use such data to optimize CRT. In other words, the IMD 16 may transmit data based on the impedance signal data to an external device such that a clinician may use the data for diagnostic purposes, followup visit adjustment, therapy adjustment (e.g., CRT adjustment), etc. For example, a clinician may use transmitted data to optimize CRT provided by the IMD 16 (e.g., modifying or adjusting the AV and/or VV delays).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
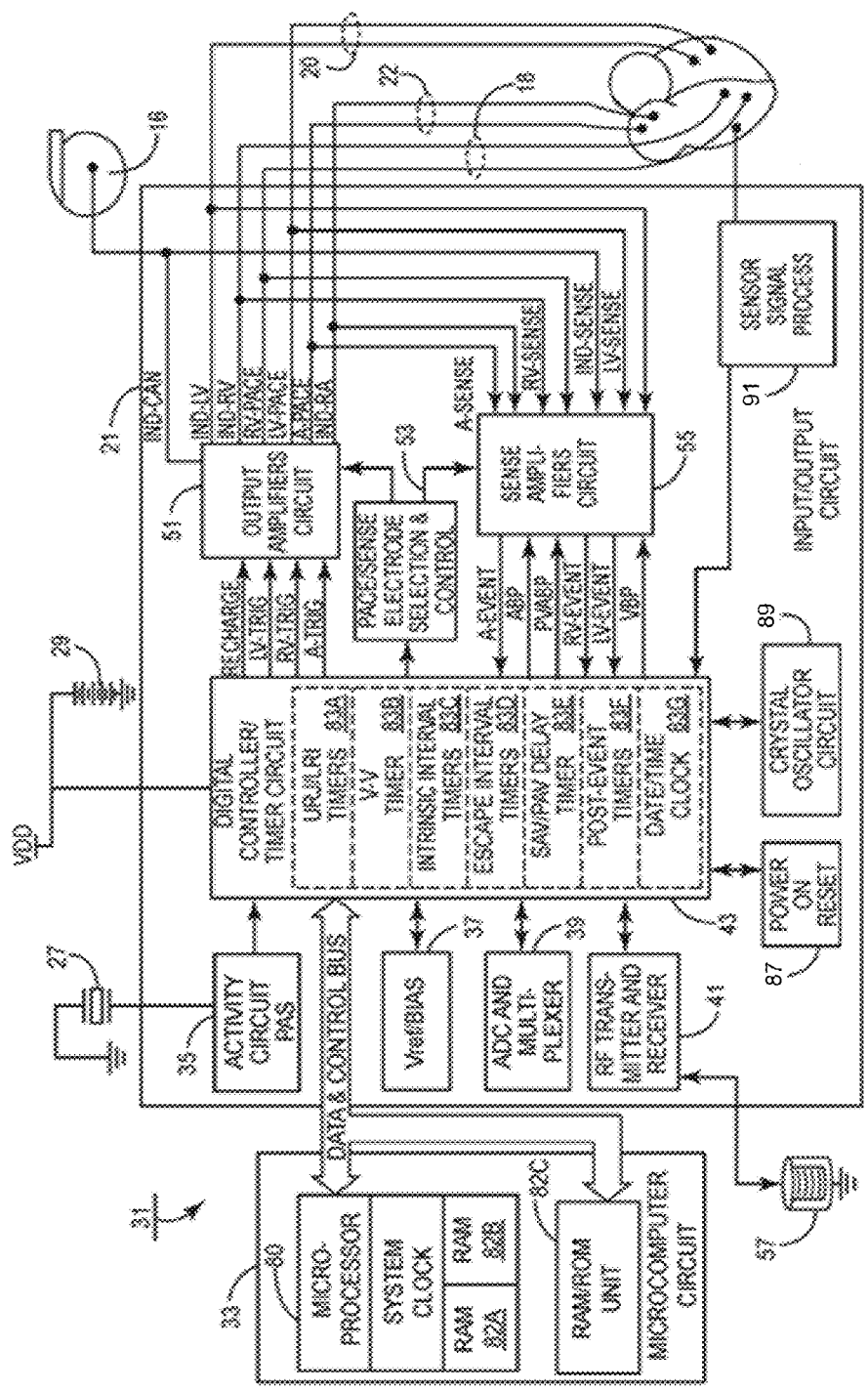
FIG. 3B is another block diagram of an exemplary IMD (e.g., an implantable pulse generator) circuitry and associated leads employable in a system such as shown in FIGS. 1-2 for providing multiple sensing channels and corresponding pacing channels.

FIG. 3B is another embodiment of a functional block diagram for IMD 16. FIG. 3B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry of cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" issued on Oct. 1, 1991 and U.S. Pat. No. 4,428,378 entitled "RATE ADAPTIVE PACER" issued on Jan. 31, 1984, each of which are incorporated herein by reference in their entireties.

Similarly, the exemplary systems, apparatus, and methods described herein may be practiced in conjunction with alternate types of sensors such as oxygenation sensors, pressure sensors, pH sensors and respiration sensors, all well known for use in providing pacing capabilities. For example, at least in one embodiment, respiration may be sensed using measurements of transthoracic impedance (e.g., impedance between an electrode implanted in the heart and an electrode on the housing of the implanted device, such as, for example, by measuring a voltage between electrode 40 and electrode 58); may be sensed using EGM derived respiration (e.g., which may be derived from the change in the amplitude of the far-field EGM, for example, sensed by electrode 66 and 58, due to respiration); respiratory signals may be acquired through the selected electrode vector configuration in an effort to measure: respiratory rate, respiratory tidal volume, inspiratory effort, and expiratory effort; etc.

Further, acoustic sensors (not shown) may be used as described herein (e.g., to detect heart sounds), or other sensors (e.g., for detection of valve closures) may be used, with such signals representative thereof being adapted for use by the IPG circuit 31. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

In one or more embodiments of the methods and/or devices described herein, various patient physiological parameters (e.g., intracardiac impedance, heart sounds, cardiac cycle intervals such as R-R interval, etc.) may be monitored for use in acquiring selection data to optimize CRT (e.g., set AV and/or VV delay, optimize cardiac contractility, for example, by using and/or measuring impedance first derivative dZ/dt, select pacing site, select pacing vector, lead placement, or assess pacing capture from both the electrical and mechanical points of view (e.g., electrical capture may not mean mechanical capture, and the heart sounds and impedance may assist in assessing whether the electrical stimulus captures the heart or not by looking at the mechanical information from the heart sounds and impedance), select an effective electrode vector configuration for pacing, etc.). For example, intracardiac impedance signals between two or more electrodes may be monitored for use in providing such optimization. Exemplary generalized method 130 for use in monitoring a patient's heart and/or optimizing cardiac therapy (e.g., setting device parameters, adjusting device parameters, initializing device parameters, etc.) is diagrammatically depicted in FIG. 4. Method 130 is intended to illustrate the general functional operation of the devices and/or systems described herein, and should not be construed as reflective of a specific form of software or hardware necessary to practice all of the methods described herein. It is believed that the particular form of software will be determined primarily by the particular system architecture employed in the device (e.g., the IMD 16) and by the monitoring and therapy delivery methodologies employed by the device and/or system. Providing software and/or hardware to accomplish the described methods in the context of any modern IMD, given the disclosure herein, is within the abilities of one of skill in the art.

Figure 4:
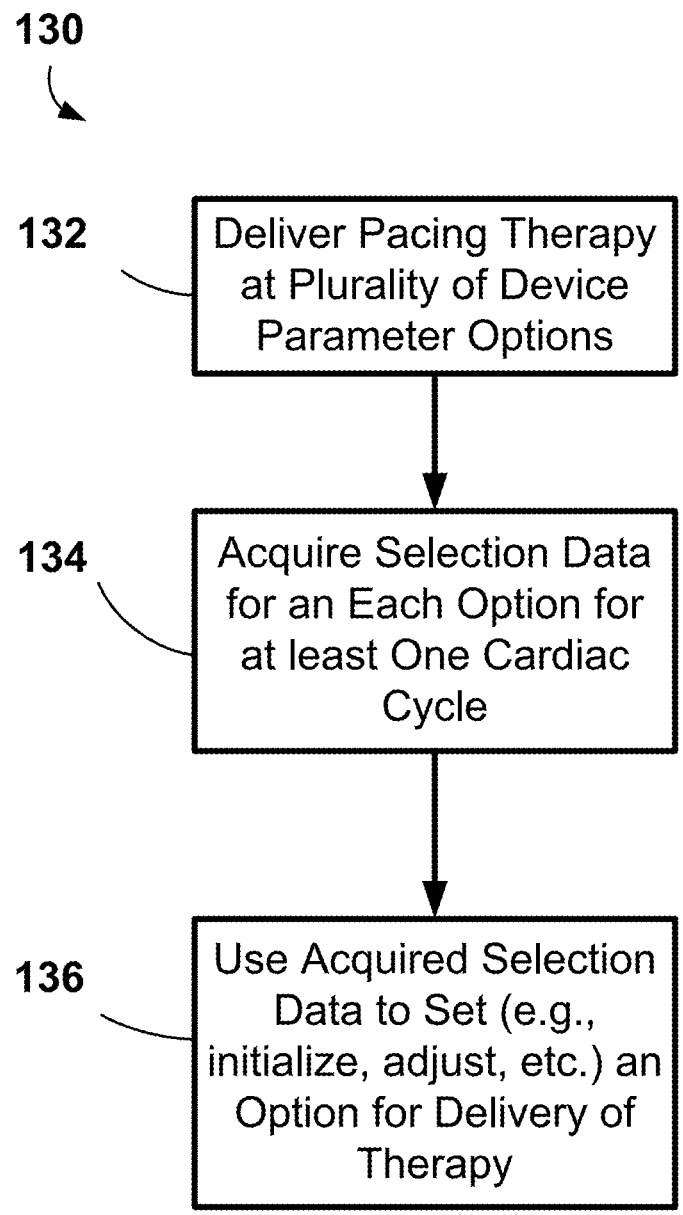
FIG. 4 is a flow chart of an exemplary method for use in optimizing a device parameter for delivering therapy to a patient's heart, e.g., using the IMD of FIGS. 1-3.

The method 130 of FIG. 4 may be generally described as a data collection process, e.g., collection of measurement data based on intracardiac impedance, for use in setting one or more device parameters. For example, the method 130 may include delivering pacing therapy (e.g., CRT therapy) at a plurality of device parameters options (block 132) (e.g., a plurality of optional AV delays, a plurality of VV delays, a plurality of electrode vector configurations, different pacing sites, different lead placements, etc. Selection data may be acquired for each option of the plurality of options (e.g., block 134) (e.g., for each optional AV delay, for each VV delay, for each optional electrode vector configuration used to pace the heart, etc.) for at least one cardiac cycle (e.g., a plurality of cardiac cycles at the end of a respiratory cycle). For example, such selection data may include various measurements extracted from intracardiac impedance signals based on temporal fiducial points associated with at least a part of a systolic portion and/or at least a part of a diastolic portion of the cardiac cycle (e.g., temporal fiducial points determined in one or more various manners, such as with use of detected heart sounds using an acoustic sensor, with use of minimum and maximum impedance signal detection, with use of one or more algorithms applied to a physiological parameter such as R-R interval, etc.).

After collection or acquisition of such selection data (block 134) for each device parameter option, the selection data may be used to set (e.g., initialize, adjust, reset, apply, etc.) one optional device parameter of the plurality of optional device parameters for delivery of therapy (block 136) (e.g., CRT). For example, the selection data may be used in a scoring algorithm to determine which of the device parameter options would provide better CRT results than others (e.g., which device parameter would provide optimal results). For example, one or more scoring techniques will be described herein with respect to selection of an optimal AV delay (see, e.g., FIGS. 23-24).

Figure 5:
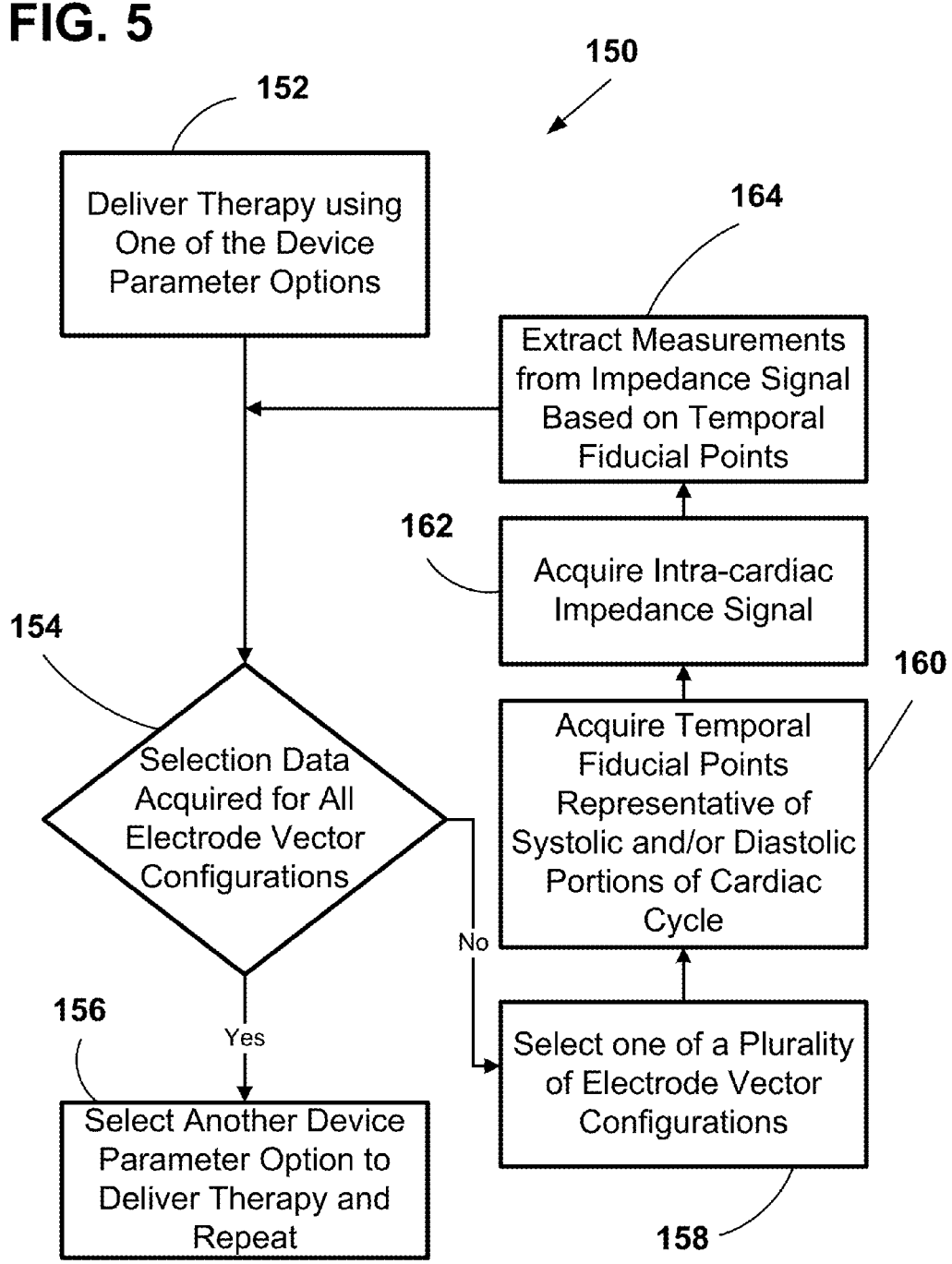
FIG. 5 is a flow chart of an exemplary method for use acquiring selection data as shown generally, for example, in the method of FIG. 4.

FIG. 5 shows one exemplary embodiment of a method 150 for acquiring selection data for one of the device parameter options (e.g., one of the selectable device parameters that may be used to optimize CRT, such as a potential AV delay that may be an optimal parameter). For example, as shown in FIG. 5, pacing therapy is delivered using one of the plurality of device options (block 152) (e.g., the plurality of device parameter options may be selected, determined and/or calculated AV delays, such as percentages of intrinsic AV delay, for example, 40% of intrinsic AV delay, 50% of intrinsic AV delay, 60% of intrinsic AV delay, 70% of intrinsic AV delay, 80% of intrinsic AV delay, etc.). For the device parameter option used to pace (block 152), selection data is acquired at each of a plurality of electrode vector configurations (e.g., intracardiac impedance is monitored over a plurality of cardiac cycles and selection data is extracted using such impedance signal). As indicated by the decision block 154, if selection data has not been acquired from all desired electrode vector configurations, then the loop of acquiring selection data (e.g., the loop illustrated by blocks 158, 160, 162, and 164) is repeated. If selection data has been acquired from all desired electrode vector configurations, then another different device parameter option is used to deliver therapy and the method 150 of FIG. 5 is repeated (e.g., for the different device parameter option) until selection data has been acquired for all the different device parameter options (e.g., selection data being collected at each of a plurality of electrode vector configurations for each of the different device parameter options).

As shown in the repeated loop of acquiring selection data for each of the desired electrode vector configurations (e.g., blocks 158, 160, 162, and 164), one of the plurality of electrode vector configurations is selected for use in acquiring selection data (block 158). Temporal fiducial points associated with at least a part of a systolic portion of at least one cardiac cycle and/or temporal fiducial points associated with at least a part of a diastolic portion of at least one cardiac cycle for the selected electrode vector configuration are acquired (block 160) (e.g., such as with use of heart sounds, analysis of impedance signal minimum and maximums, application of algorithms based on physiological parameters such as R-R intervals, etc.). For example, temporal fiducial points associated with the systolic and/or diastolic portions of the cardiac cycle may be acquired, temporal fiducial points associated with one or more defined segments within systolic and/or diastolic portions of the cardiac cycle may be acquired, and/or temporal fiducial points within or associated with one or more points and/or portions of a systolic and/or diastolic portion of the cardiac cycle may be acquired. Yet further, for example, temporal fiducial points associated with just the systolic portion or just the diastolic portion of the cardiac cycle may be acquired, temporal fiducial points associated with one or more defined segments within just the systolic portion or just the diastolic portion of the cardiac cycle may be acquired, and/or temporal fiducial points within or associated with one or more points and/or portions of just the systolic portion or just the diastolic portion of the cardiac cycle may be acquired. In other words, fiducial points may be acquired that are associated with either both the systolic and diastolic portions of the cardiac cycle or associated with just one of such portions of the cardiac cycle. Further, for example, such fiducial points may be representative or indicative of a measurement window and/or time period (e.g., interval, point, etc.) at or during which intracardiac impedance may be measured for use in analysis as described herein.

In about the same timeframe (e.g., about simultaneously with the acquired fiducial points), an intracardiac impedance signal is acquired at the selected electrode vector configuration (block 162). With the acquired fiducial points and the acquired intracardiac impedance signal, measurements from the impedance signal are extracted based on the temporal fiducial points (block 164) (e.g., integral of the impedance signal in a measurement window defined between fiducial points, maximum slope of impedance signal in a measurement window defined between fiducial points, time between the fiducial points, maximum impedance at a fiducial point, etc.). One or more of such measurements may be comparable to desired values for such measurements allowing for a determination of whether the measurement may indicate that the device parameter option may be an effective device parameter for optimizing therapy (e.g., a scoring algorithm may be used to determine if a device parameter option may be an optimal parameter based on whether a plurality of such measurements meet certain criteria or thresholds).

The measurement data for each of the device parameter options (e.g., obtained such as described in FIG. 5) is determined for at least one cardiac cycle. In one or more embodiments, such measurement data is acquired for a plurality of cardiac cycles. The cardiac cycles during which measurement data is acquired may be any suitable cardiac cycle. In one or more embodiments, the selected cardiac cycles during which measurement data is acquired is based on the respiratory cycle. In at least one embodiment, the measurement data is acquired during cardiac cycles occurring at the end of a respiratory cycle (e.g., proximate the end of expiration).

Figure 6:
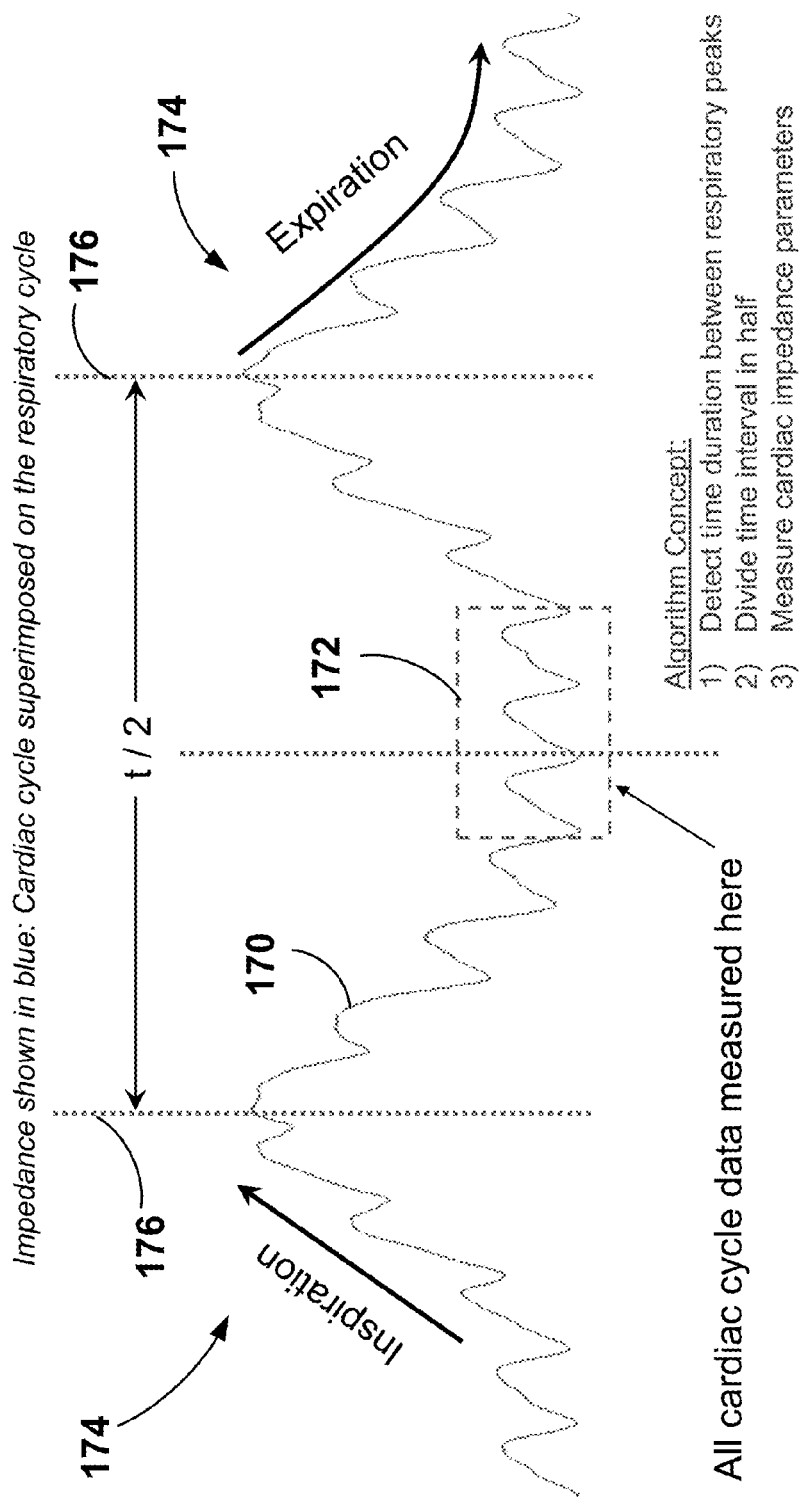
FIG. 6 is an exemplary graphical depiction of impedance waveforms over a plurality of cardiac cycles superimposed on respiratory cycles for use in describing one or more exemplary methods such as shown, for example, in FIG. 5.

For example, FIG. 6 is illustrative of one embodiment of an algorithm for selection of cardiac cycles during which the measurements may be made. An objective of the algorithm illustrated in FIG. 6 is to determine a three (3) cardiac cycle measurement window at the end of expiration to allow for measurement of predefined impedance parameters (e.g., via an electrode vector configuration, such as for a particular device parameter option). FIG. 6 depicts a measurement window acquired at the end of the respiratory cycle for a three-beat assessment of cardiac function (e.g., at particular pacing delivered using a device parameter option). The impedance signal acquired at each vector configuration for each device parameter option undergoes the three-beat analysis and selection data derived from the measurements may be used to set an optimized device parameter (e.g., the measurements may be compared within the electrode vector configuration and between other vector configurations to optimize device parameters for CRT).

FIG. 6 shows an impedance signal 170 acquired over multiple cardiac cycles (e.g., box 172 showing the impedance signal 170 over a three cardiac cycle window) superimposed on multiple respiratory cycles 174 (e.g., two respiratory cycles being shown illustratively in FIG. 6). The respiratory cycles 174 may be monitored in any suitable manner such as described herein (e.g., monitoring of transthoracic impedance signals) to determine the end of respiration such that multiple cycles proximate the end of respiration may be selected for the measurement of data. In one embodiment as shown in FIG. 6, the location of cardiac cycles during which measurements are made may be determined by detecting respiratory peaks 176 and/or the time duration between such respiratory peaks 176, and then locating a region of time in a midway region between such respiratory peaks 176 representative of the end of the respiration cycle (e.g., the end of expiration). For example, the detected duration between respiratory peaks 176 may be divided in half to locate the midway region and the impedance signal 170 over multiple cardiac cycles within or proximate to the midway region (e.g., the signal in box 172) may be selected for use in providing measurement data (e.g., cardiac impedance parameters). One will recognize that other methods of selecting particular cardiac cycles over which the measurements are made may be used, for example, based on the respiration cycle and/or other physiological data.

One skilled the art will recognize that any number of device parameters may be optimized in a manner such as that described herein (e.g., AV delay, VV delay, pacing vector, pacing site, pacing vector, lead placement, assessment of pacing capture from both the electrical and mechanical points of view (e.g., electrical capture may not mean mechanical capture, and the heart sounds and impedance may assist in assessing whether the electrical stimulus captures the heart or not by looking at the mechanical information from the heart sounds and impedance), etc.) For simplicity purposes, optimization of AV delay shall be described in detail herein. However, any of the processes described herein may be used to optimize any of the other device parameters in a similar manner (e.g., the optimization of VV delay may be similar to the optimization of the AV delay).

Figure 7:
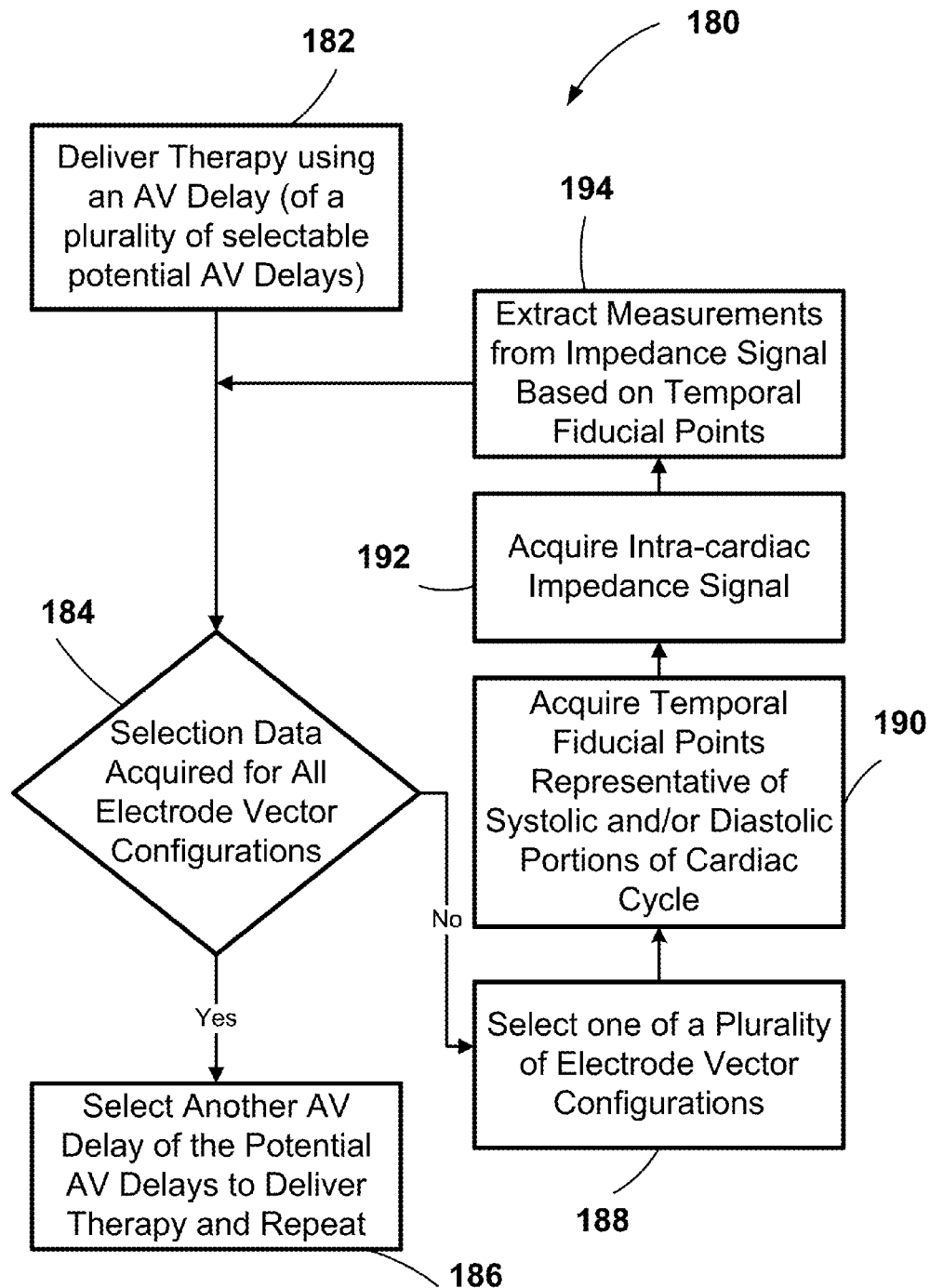
FIG. 7 is a flow chart of an exemplary method for use acquiring selection data for optimizing AV delay as shown generally, for example, in the method of FIG. 4.

For example, FIG. 7 shows one exemplary embodiment of a method 180 for acquiring selection data for one AV delay of a plurality of selectable potential AV delays that may be used to optimize CRT. As described herein, the method 180 is repeated for each potential AV delay that may possibly be set as the optimal parameter. For example, as shown in FIG. 7, pacing therapy is delivered using one of a plurality of AV delays (block 182) (e.g., the plurality of AV delays may be selected, determined and/or calculated AV delays, such as percentages of intrinsic AV delay, for example, 40% of intrinsic AV delay, 50% of intrinsic AV delay, 60% of intrinsic AV delay, 70% of intrinsic AV delay, 80% of intrinsic AV delay, etc.). The user may be allowed to set a window of allowable optional AV delays. For example, during an initial programming of the device, a user may set a parameter thereof allowing only for optional AV delays within a range, for example, 40% to 80% of intrinsic AV conduction time.

For a particular AV delay (e.g., a selected 40% of intrinsic AV delay) used to pace (block 182), selection data is acquired at each of a plurality of electrode vector configurations (e.g., intracardiac impedance is monitored over a plurality of cardiac cycles and selection data is extracted using such impedance signal). As indicated by the decision block 184, if selection data has not been acquired from all desired electrode vector configurations, then the loop of acquiring selection data is repeated (e.g., blocks 188, 190, 192, and 194). If selection data has been acquired from all desired electrode vector configurations, then another AV delay option is used to deliver therapy and the method 180 of FIG. 7 is repeated (e.g., for a different AV delay) until selection data has been acquired for all the potential different AV delay options (e.g., selection data being collected at each of a plurality of electrode vector configurations for each of the AV delays). One will recognize that the electrode vector configuration may be set first followed by proceeding to evaluate all of the device parameter options at the particular electrode vector configuration, and then another different electrode vector configuration may be set followed by collecting measurements to evaluate all of the device parameter options at the newly set electrode vector configuration, and so forth. At least in one embodiment, measurements are made for each device parameter option at each desired electrode vector configuration.

As shown in the repeated loop of acquiring selection data for each of the desired electrode vector configurations (e.g., blocks 188, 190, 192, and 194), one of the plurality of electrode vector configurations is selected for use in acquiring selection data (block 188). Temporal fiducial points associated with at least a part of a systolic portion of at least one cardiac cycle and/or temporal fiducial points associated with at least a part of a diastolic portion of the at least one cardiac cycle for the selected electrode vector configuration are acquired (block 190) (e.g., such as with use of heart sounds, analysis of impedance signal minimum and maximums, application of algorithms based on physiological parameters such as R-R intervals, etc.). In about the same timeframe (e.g., about simultaneously with the acquired fiducial points), an intracardiac impedance signal is acquired at the selected electrode vector configuration (block 192). With the acquired fiducial points and the acquired intracardiac impedance signal, measurements from the impedance signal are extracted based on the temporal fiducial points (block 194) (e.g., integral of impedance signal between fiducial points, maximum slope of impedance signal between fiducial points, time between the fiducial points, etc.).

One or more of such measurements may be comparable to desired values for such measurements allowing for a determination of whether the measurement may indicate that the AV delay option may be an effective AV delay for optimizing therapy (e.g., CRT) (e.g., a scoring algorithm may be used to determine if an AV delay may be an optimal AV delay based on whether a plurality of such measurements meet certain criteria or thresholds). The measurement for each of the AV delay options may be acquired for one or more cardiac cycles selected, such as described with reference to FIG. 6 (e.g., at the end of expiration in the respiratory cycle).

The extraction of measurements from the intracardiac impedance signal for each of the plurality of electrode vector configurations based on the temporal fiducial points and associated with at least a part of the systolic portion of at least one cardiac cycle and/or associated with at least a part of the diastolic portion of the at least one cardiac cycle (e.g., selection data acquisition loop including 158, 160, 162, and 164 as shown in FIG. 5 or selection data acquisition loop including 188, 190, 192, and 194 as shown in FIG. 7) may be implemented in one or more manners (e.g., using one or more algorithms in accordance with the functionality described herein). For example, a method to optimize AV and/or VV intervals (e.g., which are part of a collective group of CRT optimization device parameters) detects relative or absolute changes in chamber blood volume and/or chamber dimensions, isovolumic contraction and ejection times and isovolumic relaxation and filling times, based on selected measurements from impedance waveform morphologies such as a magnitude delta between impedance waveform fiducial points, a time duration between impedance waveform fiducial points, positive and negative slopes between impedance waveform fiducial points, an integral between impedance waveform fiducial points, an area between impedance waveform fiducial points, other deviations in the waveform morphology to assess hemodynamic parameters such as end diastolic volume/dimension, end systolic volume/dimension and stroke volume, isovolumic contraction and relaxation times, ejection and filling times (e.g., such as those that are conventionally measured with echocardiography methods to optimize CRT), etc.

For example, as described herein, one exemplary algorithm defines a method that measures defined parameters between fiducial points on intracardiac impedance waveform morphologies acquired from separate electrode vector configurations. Information acquired from each electrode vector configuration may be tabulated and an optimal AV and/or VV delay setting may be determined based on a composite scoring process from all impedance electrode vector configurations. For example, measurements acquired between impedance waveform fiducial points may include impedance minimum and maximums, time duration, integral, slope and the like to provide closed loop feedback on cardiac cycle ejection and filling periods. In this exemplary algorithm, cardiac cycle ejection encompasses isovolumic contraction and ejection, which is approximately 40% of the cardiac cycle duration whereas the remaining 60% of the cardiac cycle duration is comprised of isovolumic relaxation and diastolic filling as shown in FIG. 9.

Figure 8:
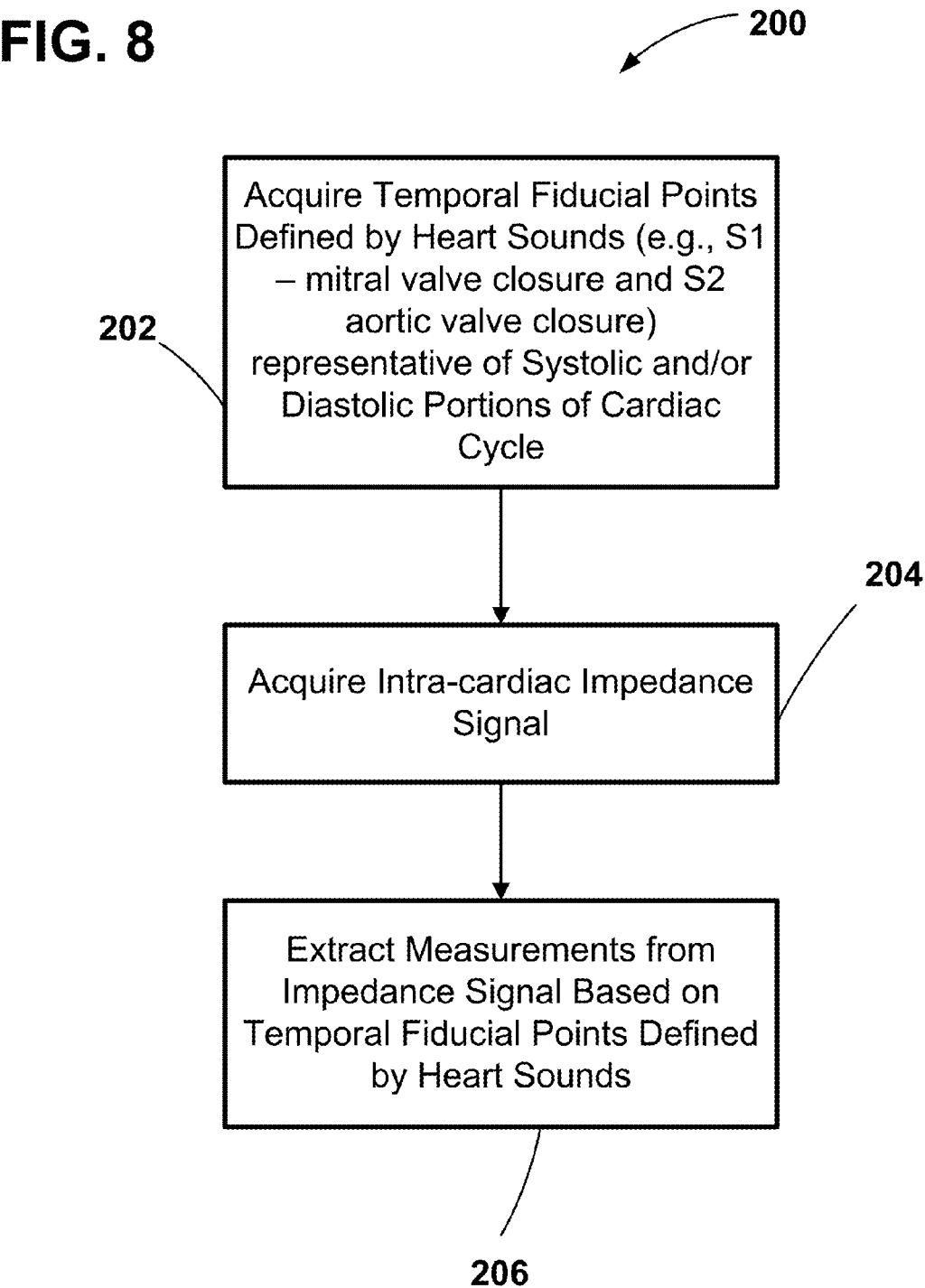
FIG. 8 is a flow diagram of an exemplary embodiment of a portion of the method of FIG. 7 including acquisition of temporal fiducial points.

FIG. 8 shows one embodiment of an exemplary method 200 to extract measurements from the intracardiac impedance signal for each of the plurality of electrode vector configurations based on the temporal fiducial points and associated with the systolic portion of at least one cardiac cycle and/or associated with the diastolic portion of the at least one cardiac cycle. The method 200 extracts measurements based on temporal fiducial points defined by the valve closures (e.g., measurement windows defined by heart sounds). For example, temporal fiducial points defined by heart sounds (e.g., S1—mitral valve closure/tricuspid valve closure and S2 aortic valve closure/pulmonary valve closure as shown in FIG. 9) associated with at least a part of systolic and/or diastolic portions of at least one cardiac cycle may be acquired (block 202) (e.g., temporal fiducial points associated with the systolic and/or diastolic portions). For example, heart sounds that may define temporal fiducial points are described in the reference, Guyton and Hall, *Textbook of Medical Physiology*, pp. 265-268 (2011 12$^{th}$ Ed.) which is incorporated by reference herein in its entirety.

About simultaneously with the acquired fiducial points, an intracardiac impedance signal is acquired at a selected electrode vector configuration (block 204). With the acquired fiducial points and the acquired intracardiac impedance signal, measurements from the impedance signal may be extracted based on the temporal fiducial points defined by the heart sounds (block 206).

Figure 9:
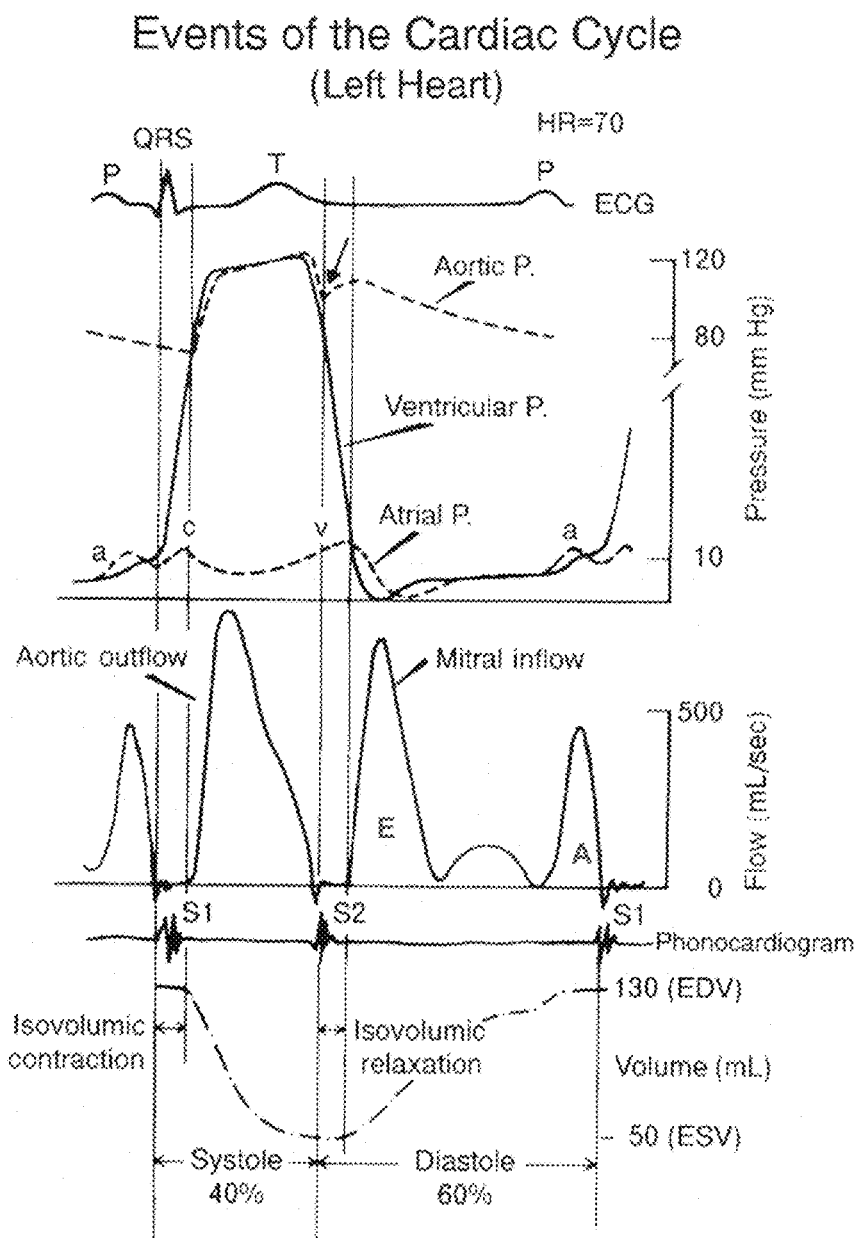
FIG. 9 is an exemplary graphical depiction of cardiac cycle events for use in describing one or more exemplary methods such as shown, for example, in FIG. 8.

FIG. 9 shows a diagram depicting events of the cardiac cycle for the left heart. One area of interest in optimizing device parameters is the systolic ejection period between heart sounds S1—mitral valve closure (MVC) and S2—aortic valve closure (AVC) encompassing isovolumic contraction and ejection. This period occupies 40% of the cardiac cycle. Subsequently, the diastolic filling period (between heart sound S2 and the following cardiac cycle's S1 heart sound) occupies the remaining 60% of the cardiac cycle. In one or more embodiments, impedance waveform measurements within these two periods or the ratio derived thereof, may be used to optimize CRT.

Fiducial points of interest that are detectable as described herein (e.g., using acoustic sensors) include S1 (MVC) and S2 (AVC). These points may be associated with impedance waveform minimum and maximum points, respectively, thus encompassing the ejection or systolic portion of the cardiac cycle. Moreover, the use of heart sounds S1 and S2 further aid in defining the ejection portion of the cardiac cycle and may be used to determine a time interval for impedance waveform measurements. The impedance waveform maximum and thus its associated heart sound S2 determine the end of the systolic portion of the cardiac cycle and the start of the diastolic filling portion of the cardiac cycle. Likewise, heart sound S1 determines the end of the diastolic portion of the cardiac cycle and the start of the systolic out flow portion of the cardiac cycle. Therefore, the heart sounds S1 and S2 can be used to determine the time intervals for impedance waveform measurements for the systolic and/or diastolic periods of the cardiac cycle. In other words, the heart sounds S1 and S2 may be used as temporal fiducial points (e.g., to define a measurement window during which one or more measurements are extracted from the impedance signal, such as, for example, positive and/or negative slopes between the heart sounds S1 and S2 of a cardiac cycle, positive and/or negative slopes between the heart sound S2 of a first cardiac cycle and a heart sound S1 of a subsequent cardiac cycle, an integral of the impedance signal between heart sounds, etc.).

Figure 10:
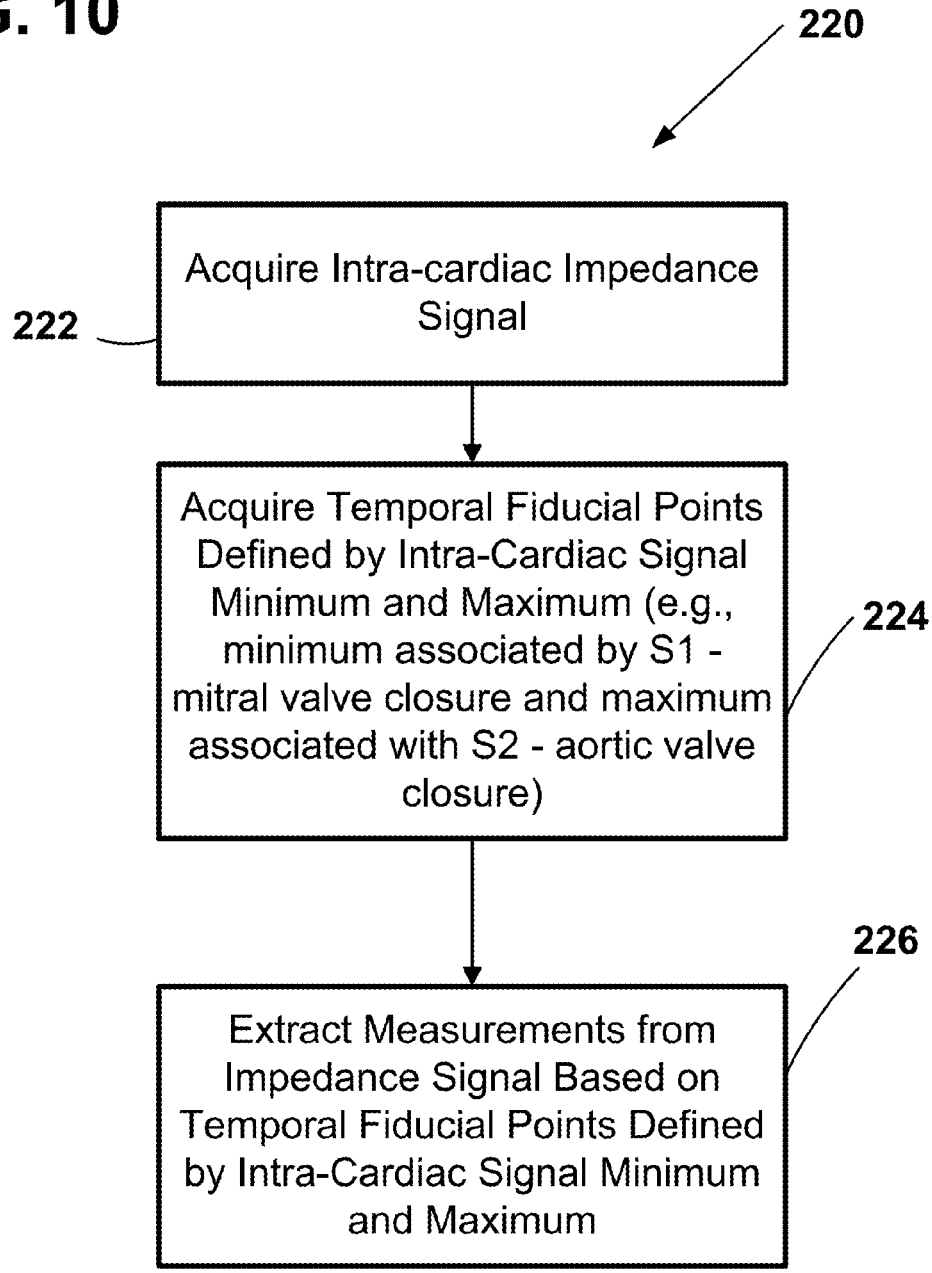
FIG. 10 is another flow diagram of an exemplary embodiment of a portion of the method of FIG. 7 including acquisition of temporal fiducial points.

FIG. 10 shows an embodiment of another exemplary method 220 to extract measurements from the intracardiac impedance signal for each of the plurality of electrode vector configurations based on the temporal fiducial points and associated with the systolic portion of at least one cardiac cycle and/or associated with the diastolic portion of the at least one cardiac cycle. The method 220 includes acquiring an intracardiac impedance signal (block 222) and then extracts measurements based on temporal fiducial points defined by the intracardiac impedance signal minimum and maximum (block 224) (e.g., points of the signal associated with and/or corresponding to heart sounds S1 and S2). For example, the temporal fiducial points defined by the minimum and maximum points of the intracardiac impedance signal (e.g., such as shown, for example, in FIG. 11, which are substantially aligned with the beginning and end of the systolic and diastolic portions of the cardiac cycle) associated with at least a part of systolic and/or diastolic portions of at least one cardiac cycle may be acquired (block 224) (e.g., temporal fiducial points associated with the systolic and/or diastolic portions). In addition, with the acquired fiducial points and the acquired intracardiac impedance signal, measurements from the impedance signal may be extracted based on the temporal fiducial points defined thereby (block 226).

The method 220 (e.g., a selection data acquisition or measurement algorithm) relies on the concept that the ejection period is primarily associated with the time duration between the impedance waveform minimum and maximum, whereas the filling period is primarily associated with the impedance waveform maximum to subsequent impedance minimum on the following cardiac cycle. Therefore, dividing the impedance waveform cardiac cycle into systolic and diastolic periods based on the impedance waveform minimum and maximum fiducial points, and measuring, for example, the time interval between the impedance waveform minimum and maximum points, the positive and negative slopes of the signal between the impedance waveform minimum and maximum points, and the integral of the signal between the impedance waveform minimum and maximum points, can be used independently or as one or more derived ratios to determine optimal CRT settings.

Figure 11:
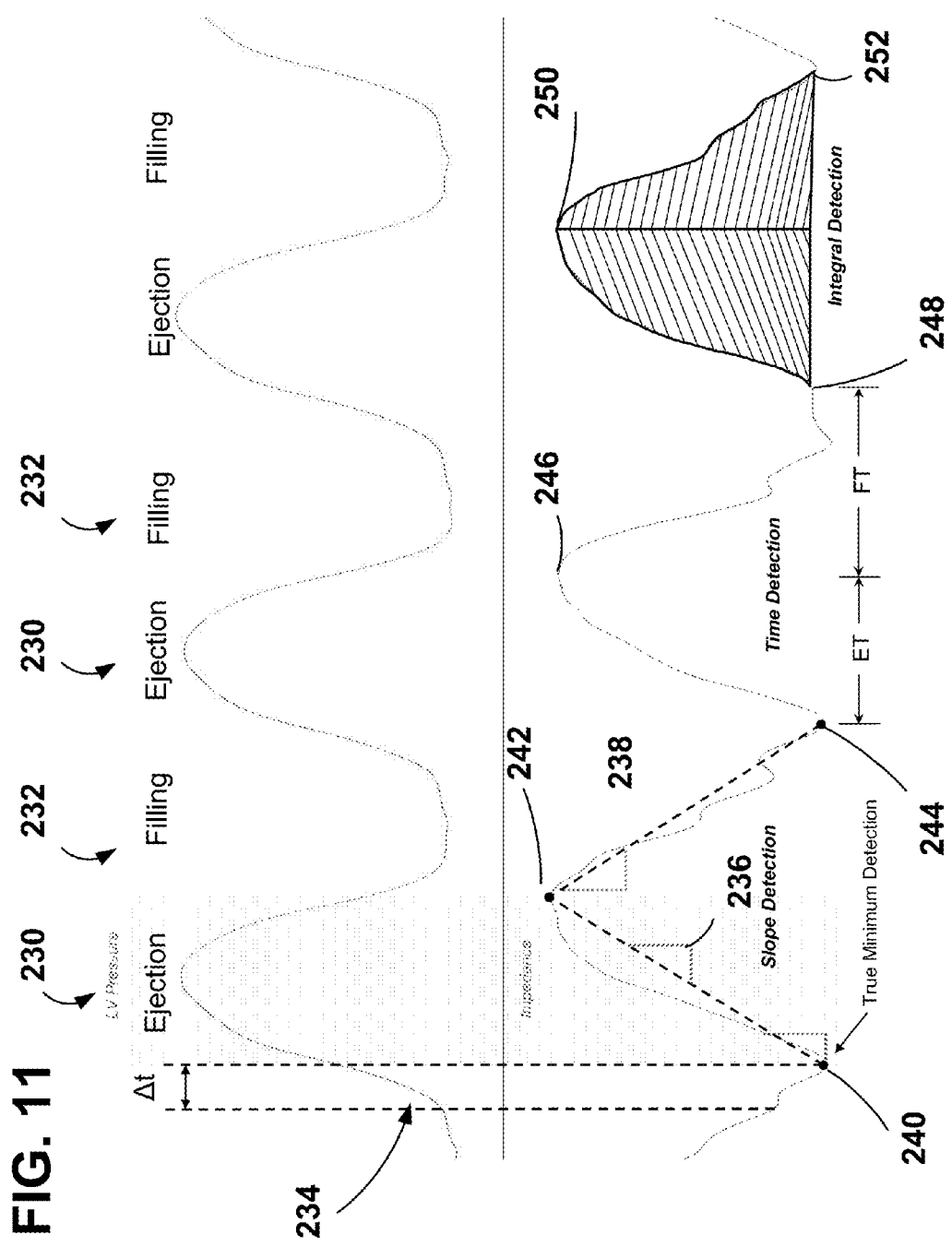
FIG. 11 is an exemplary graphical depiction of impedance waveform morphology associated with ejection and filling for use in describing one or more exemplary methods such as shown, for example, in FIG. 10.

FIG. 11 depicts a method to determine the area of the impedance waveform morphology that is primarily associated with ejection 230 and the area that is primarily associated with filling 232. Shown in FIG. 11 are left ventricular (LV) pressure waveform morphology (at the top of the diagram) and the associated impedance waveform morphology (at the bottom of the diagram). There is a slight time delay (Δt) between the impedance waveform and LV pressure minimum 234. The method of acquiring measurements using the impedance minimums and maximums is based on the concept that the ejection period is primarily associated with the time duration between the impedance waveform minimum and maximum, whereas the filling period is primarily associated with the impedance waveform maximum to the subsequent impedance minimum on the following cardiac cycle. Measurements using the impedance signal based on the temporal fiducial points defined by the impedance minimum and maximum points, may be acquired (e.g., such as the positive slope 236 between the minimum 240 and maximum 242 of a cardiac cycle as shown in FIG. 11, the negative slope 238 between the maximum 242 and a subsequent impedance minimum 244 on the following cardiac cycle as shown in FIG. 11, a time duration between the minimum 244 and maximum 246 of a cardiac cycle (e.g., the ejection phase) as shown in FIG. 11, a time duration between the maximum 246 and a subsequent impedance minimum 248 (e.g., the filling phase) as shown in FIG. 11, a time duration between the minimum 244 and a subsequent impedance minimum 248 as shown in FIG. 11, an integral between the minimum 248 and maximum 250 of a cardiac cycle (e.g., the ejection phase) as shown in FIG. 11, an integral between the maximum 250 and a subsequent impedance minimum 252 (e.g., the filling phase) as shown in FIG. 11, an integral between the minimum 248 and a subsequent impedance minimum 252 as shown in FIG. 11, and/or any other measurement that may be quantitatively used to optimized CRT).

As indicated herein, detected MVC and AVC are associated with impedance waveform minimum and maximum points, respectively. As such, the use of heart sounds S1 and S2 may further aid in defining the ejection portion of the cardiac cycle and can be used as a validation sensor to determine a time interval for impedance waveform measurements (e.g., such as those based on minimum and maximum impedance). Likewise, impedance waveform minimum and maximum points may be used to validate time intervals associated with heart sounds.

Figure 12:
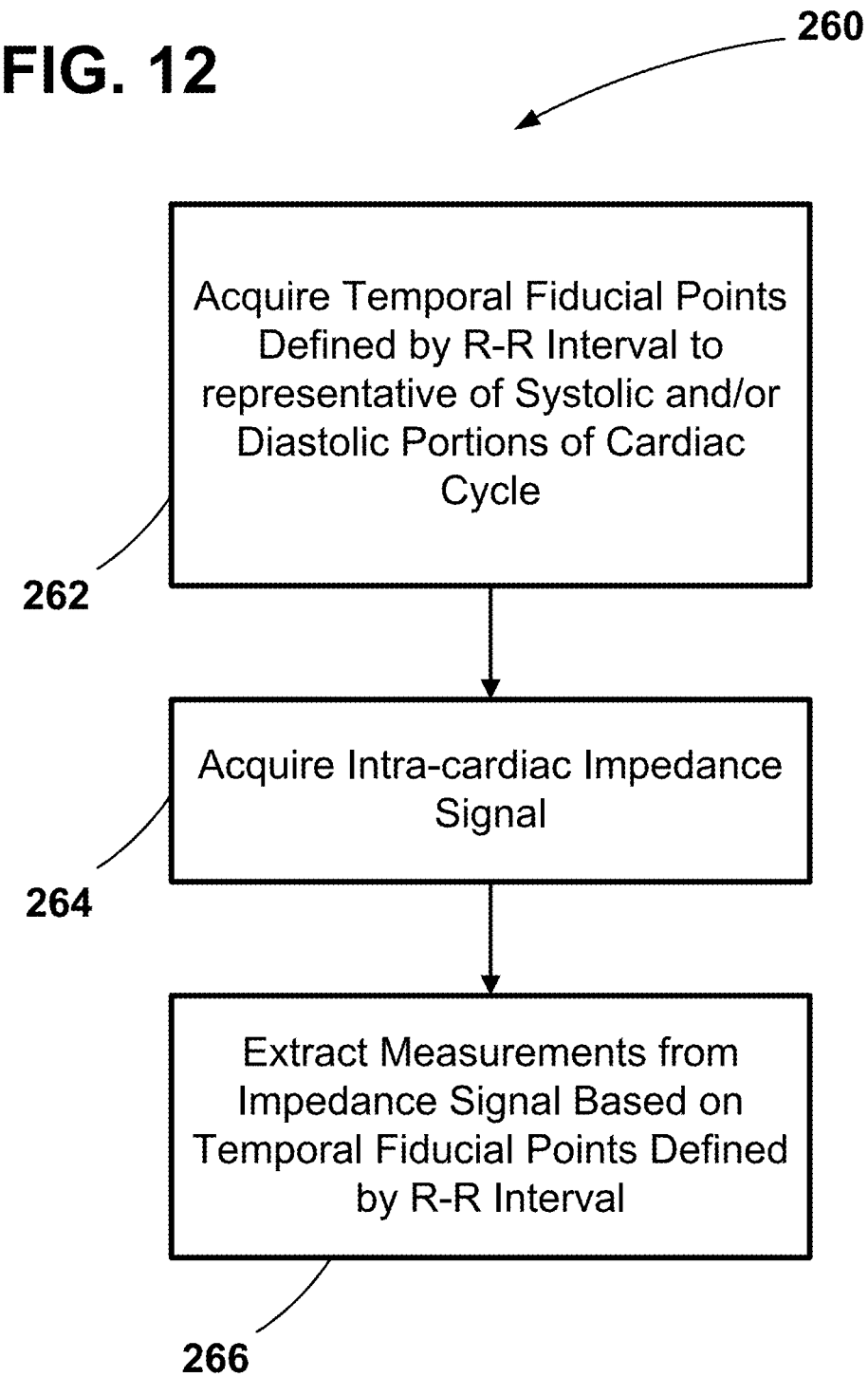
FIG. 12 is another flow diagram of an exemplary embodiment of a portion of the method of FIG. 7 including acquisition of temporal fiducial points.

FIG. 12 shows an embodiment of yet another exemplary method 260 to extract measurements from the intracardiac impedance signal for each of the plurality of electrode vector configurations based on the temporal fiducial points and associated with the systolic portion of at least one cardiac cycle and/or associated with the diastolic portion of the at least one cardiac cycle. The method 260 extracts measurements based on temporal fiducial points defined based on the R-R interval (block 262) (e.g., applying an algorithm to the R-R interval for defining portions representative of systolic and diastolic portions of the cardiac cycle). For example, temporal fiducial points associated with the systolic portion of at least one cardiac cycle may include at least points associated with a first predetermined portion of an R-R interval and/or the temporal fiducial points associated with the diastolic portion of the at least one cardiac cycle may include at least points associated with a second predetermined portion of the R-R interval.

About simultaneously with the acquired fiducial points, an intracardiac impedance signal is acquired at a selected electrode vector configuration (block 264). With the acquired fiducial points based on the R-R interval and the acquired intracardiac impedance signal, measurements from the impedance signal may be extracted based thereon (block 266).

The method described with reference to FIGS. 10-11 may be effective for collecting data in a setting where the impedance waveform minimum and maximum are clearly defined. However, in a setting where the impedance waveform may contain multiple peaks as shown in the impedance waveform of FIG. 13 (the waveform at the bottom), the method 260 of FIG. 12 based on R-R interval may rather be used (e.g., an algorithm or subroutine that defines a portion of the R-R interval as the impedance waveform measurement window). For example, an R-R interval may be detected as described herein and as shown in the waveform at the top of FIG. 13 (e.g., an intrinsic R-R interval being 0.665 seconds). Accepting that a predefined percentage of the R-R interval is associated with the systolic portion of cardiac cycle and another predefined percentage of the R-R interval is associated with the diastolic portion of the cardiac cycle, then, for example, approximately 40% of the cardiac cycle (R-R interval) may be associated with systole and the remaining 60% of the cardiac cycle may be associated with diastole. As such, the fiducial points based on the R-R interval may include points associated with a first predetermined portion of the cardiac cycle (e.g., from a minimum impedance 272 to a point 274 in the cardiac cycle determined by the set percentage, such as 40%) and points associated with a second predetermined portion of the cardiac cycle (e.g., from the point 274 in the cardiac cycle determined by the set percentage, such as 40%, to the minimum impedance 276 of the subsequent cycle).

Figure 13:
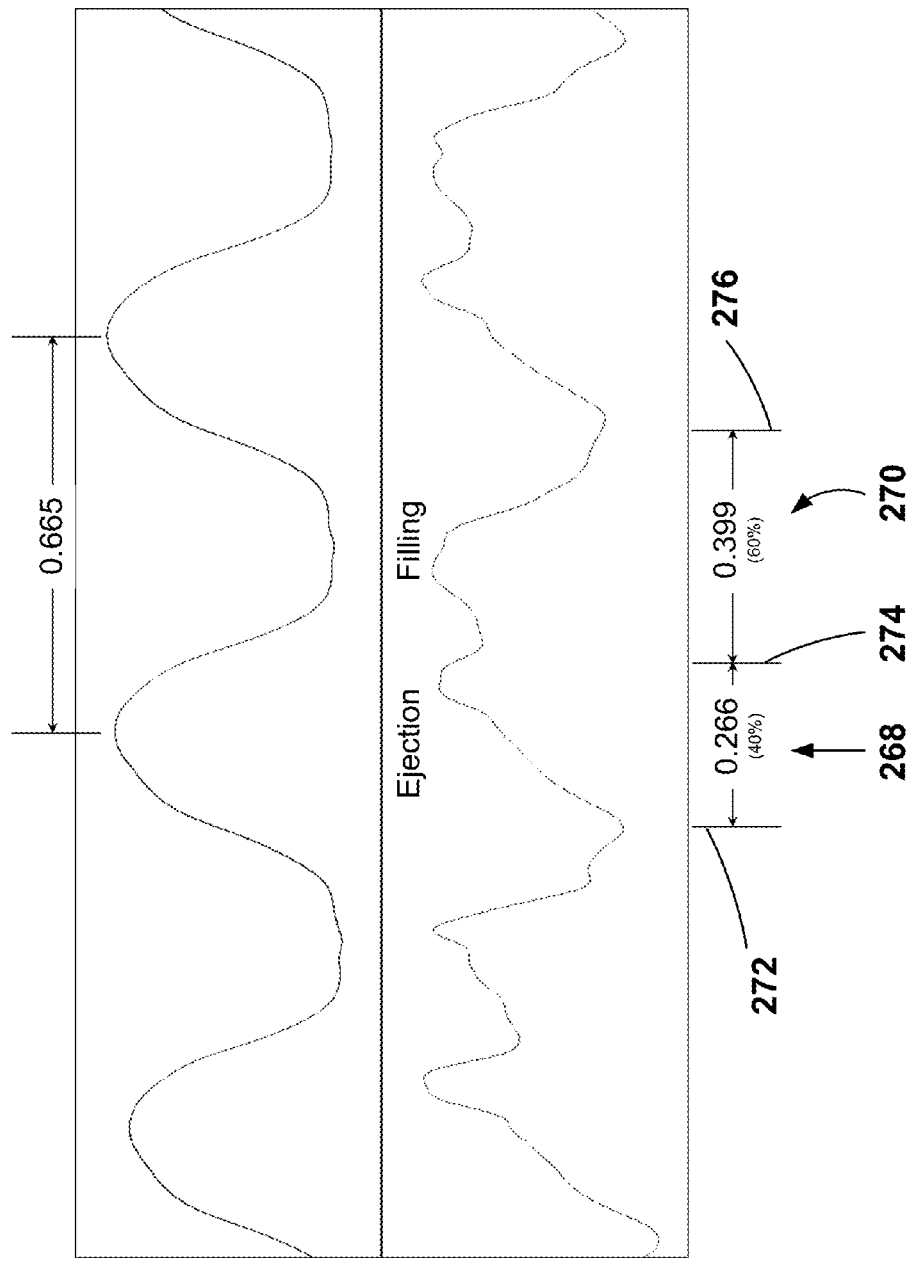
FIG. 13 is an exemplary graphical illustration relating R-R intervals to ejection and filling for use in describing one or more exemplary methods such as shown, for example, in FIG. 12.

FIG. 13 depicts the method to determine ejection periods and filling periods based on a percent time of the cardiac cycle or R-wave to R-wave interval. In this example, the R-R interval is 665 milliseconds. Calculating 40% of this interval may define a systolic period of 266 milliseconds and a diastolic period of 399 milliseconds. Impedance parameters can be measured (e.g., those described above with reference to FIG. 10-11) between these intervals for CRT optimization (e.g., intervals 272 to 274, 274 to 276, and/or 272 to 276).

One skilled in the art will recognize that any of the methods for acquiring selection data (e.g., measurements and/or data derived from such measurements) may be used independently and/or in combination with one or more other acquisition methods. For example, the method as described with reference to FIGS. 12-13 may be used in combination with heart sounds to define measurement window intervals established by fiducial points. Further, one or more of such acquisition methods may be used to validate one or more of the other acquisition methods described herein. For example, the data acquisition method described with reference to FIGS. 10-11 using impedance minimums and maximums may be used to validate acquisition of fiducial points based on heart sounds. In other words, multiple combinations of such methods described herein may be used for collection or acquisition of selection data to set optimal device parameters for CRT.

Further, measurements extracted using the impedance signal based on the temporal fiducial points may include various measurements (e.g., positive and negative slope, integrals, etc.) usable as selection data as described herein. Selection data may be determined based upon such extracted measurements. For example, such extracted measurements may be used independently or may be used to derive one or more types of selection data therefrom (e.g., such measurements may be used to determine or calculate other useful values). For example, with reference to FIG. 11, an integral between the minimum 248 and maximum 250 of a cardiac cycle (e.g., the ejection phase) as shown in FIG. 11 may be used independently as selection data or may be used to generate a ratio with the integral between the maximum 250 and a subsequent impedance minimum 252 (e.g., the filling phase). Various types of selection data may be generated as clearly shown by the more detailed exemplary process described herein with reference to FIGS. 15-24.

Figure 14:
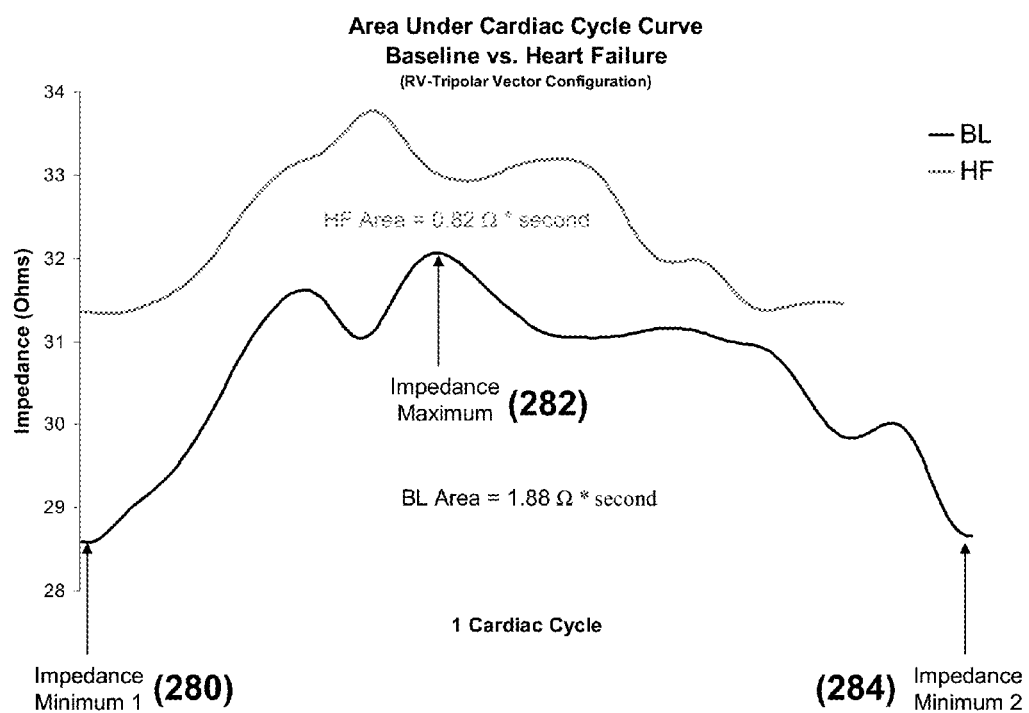
FIG. 14 is an exemplary graphical depiction of impedance waveforms over a cardiac cycle for use in describing one or more exemplary methods of acquiring selection data, such as shown, for example, in FIG. 5.

FIG. 14 depicts a full cardiac cycle measurement process that may be used to further provide additional data. The method of measurement and analysis is used to determine an impedance minimum 280, an impedance maximum 282, and an area under the impedance curve from impedance minimum 280 to a subsequent minimum 284 and integral (not shown) between the two minimum points 280, 284. This analysis depiction measures parameters per cardiac cycle rather than dividing the cardiac cycle into ejection and filling segments and making measurements for the portions of the cardiac cycle.

The diagram of FIG. 14 depicts a manner of evaluating the change in impedance based on the area under the curve measured from impedance waveform minimum 280 to the subsequent waveform minimum point 284. Data shown in this example depicts the change in impedance waveform area at baseline (BL) and at the end of 4 weeks high rate pacing in dogs (HF). The data depicts impedance waveform sensitivity to change in area under the impedance curve during sub-optimal cardiac function.

As generally provided herein with reference to FIG. 4, the method 130 includes using the acquired selection data relating to each of the plurality of options of the device parameter (e.g., AV delay) to set one option of the plurality of options for delivery of CRT to the patient. Any effective method to analyze the acquired selection data (e.g., acquired for each of a plurality of optional device parameters) and select one of the optional device parameters for use in CRT may be used. For example, such selection data may include extracted measurements from the impedance signal as described herein (e.g., slopes, integrals, areas, minimums, maximums, time durations, etc.), values derived from such extracted measurements of the impedance signal (e.g., ratios, combinations, summations, algorithm calculated values using such measurements, etc.), measurements of the impedance signal relating to the entire cardiac cycle, measurements of the impedance cycle relating to the systolic portion of the cardiac cycle, measurements relating to the diastolic portion of the cardiac cycle, and/or any other values based upon the extracted measurements of the impedance signal based on the temporal fiducial points acquired in one or more manners as described herein. The selection data may be compared to baseline data, to predetermined values, to statistically established criteria, to selection data of cardiac cycles acquired during different time periods, to selection data used to establish baseline data, to known and/or theoretical values, etc., for example, in order to determine whether the device parameter option (e.g., for which such selection data was acquired as described with reference to FIG. 5 or FIG. 7) would be an optimal parameter for delivering CRT.

The analysis of the selection data acquired for corresponding device parameter options may be compared such that a resulting optimal device parameter may be selected. For example, selection data acquired for each of a plurality of AV delays (e.g., 40% of intrinsic AV delay, 50% of intrinsic AV delay, 60% of intrinsic AV delay, and 70% of intrinsic AV delay) may be independently analyzed for each of the corresponding AV delays. Such independent analyses may then be compared to one another for selection of an optimal AV delay.

One process of performing such analysis and comparison may include one or more scoring techniques suitable to evaluate and select an optimal parameter. For example, one illustrative scoring process may include providing a score for each of the plurality of options of the device parameter (e.g., for each of 40% of intrinsic AV delay, 50% of intrinsic AV delay, 60% of intrinsic AV delay, and 70% of intrinsic AV delay) based on the acquired selection data (e.g., maximums, slopes, integrals, ratios, etc.) for each vector configuration. One of the plurality of options (e.g., 50% of intrinsic AV delay) may be selected based on the scores for the plurality of options of the device parameter for delivery of CRT to the patient.

In one or more embodiments of the scoring process, each type of selection data (e.g., maximums, slopes, integrals, ratios, etc.) may be given the same weight in the scoring process or one or more of the types of selection data may be assigned different weights dependent upon, for example, whether such type of selection data might be more accurate and/or make more contribution in determining an optimal setting. For example, selection data such as a ratio of the slope of the impedance signal during ejection to the slope of the impedance signal during filling may provide a better indicator of a more effective device parameter than just slope of the impedance signal during filling when considered independently. One will recognize that the selection data may be acquired and stored as necessary to carry out the analysis thereof and selection of an optimal device parameter.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

An exemplary algorithm for AV delay optimization shall be described with reference to FIGS. 15-24. The algorithm includes definition and use of four sub-routines. However, clearly such functionality may be implemented in many manners and the exemplary algorithm is provided to simply illustrate the various methods described herein (e.g., extraction of measurements, scoring, etc.) for optimizing AV delay. As indicated previously, similar methods may be used for optimizing other parameters, such as V-V delay.

Figure 15:
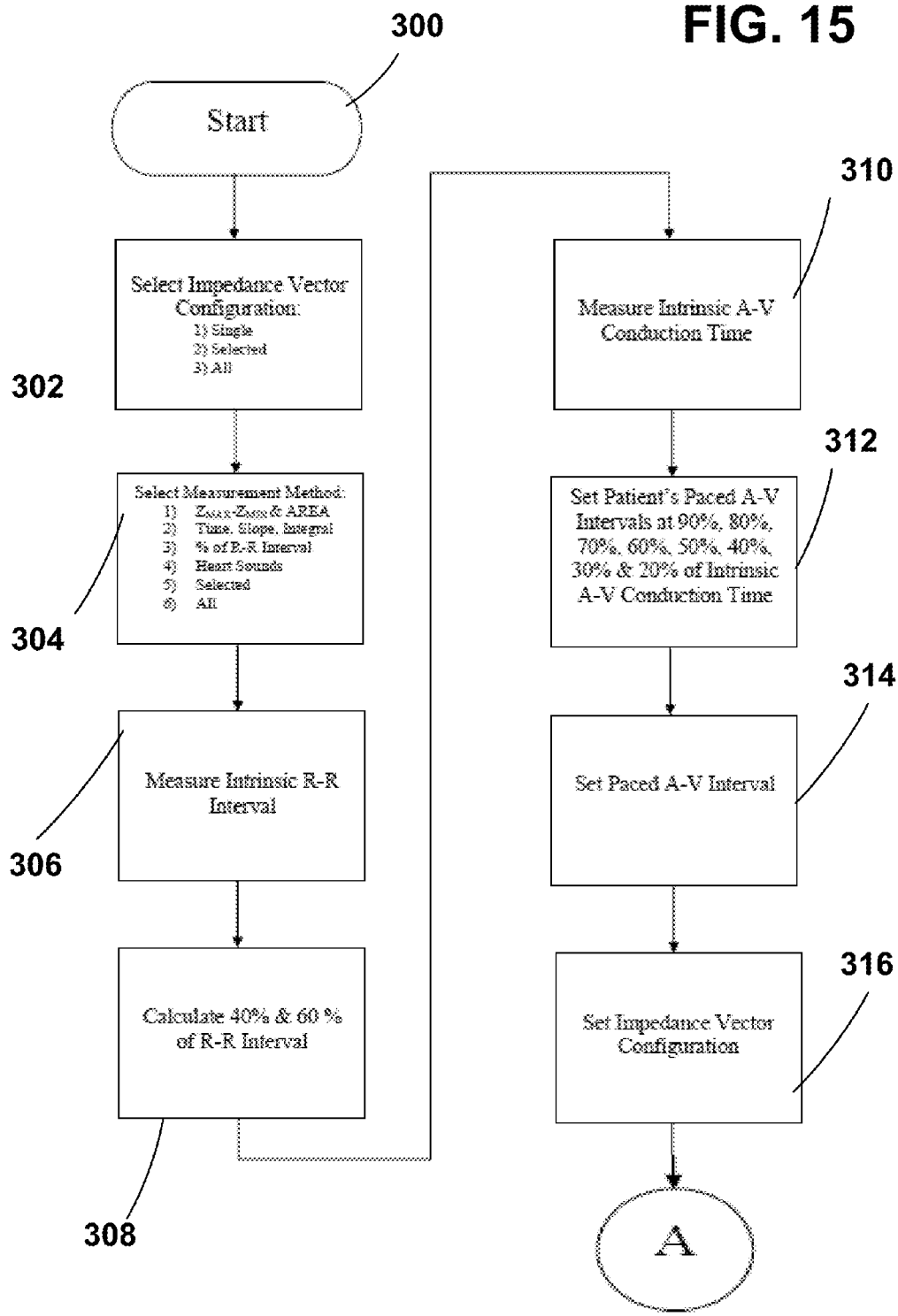
FIGS. 15-22 are flow charts of a more detailed exemplary method for optimizing AV delay as shown generally, for example, in the method of FIG. 5, including an exemplary scoring process.

The algorithm is started (block 300) and various selections for implementing the algorithm are made as shown in FIG. 15. For example, as shown in block 302, the type of impedance vector configurations may be selected. For example, a single impedance vector configuration may be selected for use, various impedance vector configurations may be selected from a plurality of available impedance vector configurations, or all available impedance vector configurations may be selected. Such selected impedance vector configurations (e.g., defined by selected electrodes as described herein) may be used for providing the intracardiac impedance signals from which measurements may be extracted.

Further, for example, as shown in block 304, one or more various types of measurement techniques may be selected. For example, one or more of the following measurement techniques relating to the impedance (Z) signal (e.g., as described with reference to FIGS. 8-14; based on one or more fiducial points; relating to intervals defined by fiducial points, etc.) may be selected for use in providing selection data: 1) $Z_{MAX}$–$Z_{MIN}$ and Area (e.g., from $Z_{MIN}$ to $Z_{MIN}$ of following cycle); 2) the Time (e.g., between fiducial points), the Slope (e.g., between $Z_{MIN}$ and $Z_{MAX}$, for example, see FIG. 11), and Integral (e.g., between $Z_{MIN}$ and $Z_{MAX}$, for example, see FIG. 11); 3) % of R-R Interval (e.g., used to provide fiducial points to establish measurement windows, for example, see FIGS. 12 and 13); and 4) Heart Sounds (e.g., S1 and S2, see FIGS. 8 and 9). As shown in block 304, any one of such measurement techniques may be selected, any one or more of such available measurement techniques may be selected (e.g., as indicated by "5) Selected"), or all of such measurement techniques may be selected (e.g., as indicated by "6) All").

With such selections made, measurement of intrinsic R-R interval may be performed (block 306) (e.g., for use in carrying out the process described, for example, with reference to FIGS. 12 and 13) and calculations may be performed to provide fiducial points to establish measurement windows, for example, as described with reference to FIGS. 12 and 13 (block 308). For example, such calculations may include establishing a systolic measurement window portion (e.g., 40% of the R-R interval) and/or a diastolic measurement window portion (e.g., 60% of the R-R interval).

Further, with such selections made, measurement of intrinsic AV conduction time may be performed (block 310) (e.g., for use in determining potential AV delay pacing parameters, for example, for use in providing CRT pacing such that selection data may be collected for each of such AV delay pacing parameters, in a manner such as described with reference to FIG. 7). For example, calculations may be performed to provide each of the potential optimal pacing AV intervals for which selection data may be collected in an independent manner by taking certain percentages of the intrinsic A-V conduction time (block 312), such as, for example, 20% of intrinsic AV delay, 30% of intrinsic AV delay, 40% of intrinsic AV delay, 50% of intrinsic AV delay, 60% of intrinsic AV delay, 70% of intrinsic AV delay, 80% of intrinsic AV delay, 90% of intrinsic AV delay).

As each of the potentially selectable pacing AV intervals have been defined (block 312), selection data may be acquired for one of such defined pacing AV intervals by setting it or selecting it for use to deliver pacing (block 314) and setting the one or more impedance vector configurations (block 316) to be used for acquiring signals from which measurements may be extracted (e.g., upon which selection data may be based). As will become apparent from the description below, selection data may be acquired for each of the other defined pacing AV interval options (e.g., the calculated % values of intrinsic AV conduction) by setting each of them for use to deliver pacing and setting the one or more impedance vector configurations to be used for acquiring signals from which measurements may be extracted for each of such AV interval options, independently from the other options.

Figure 16:
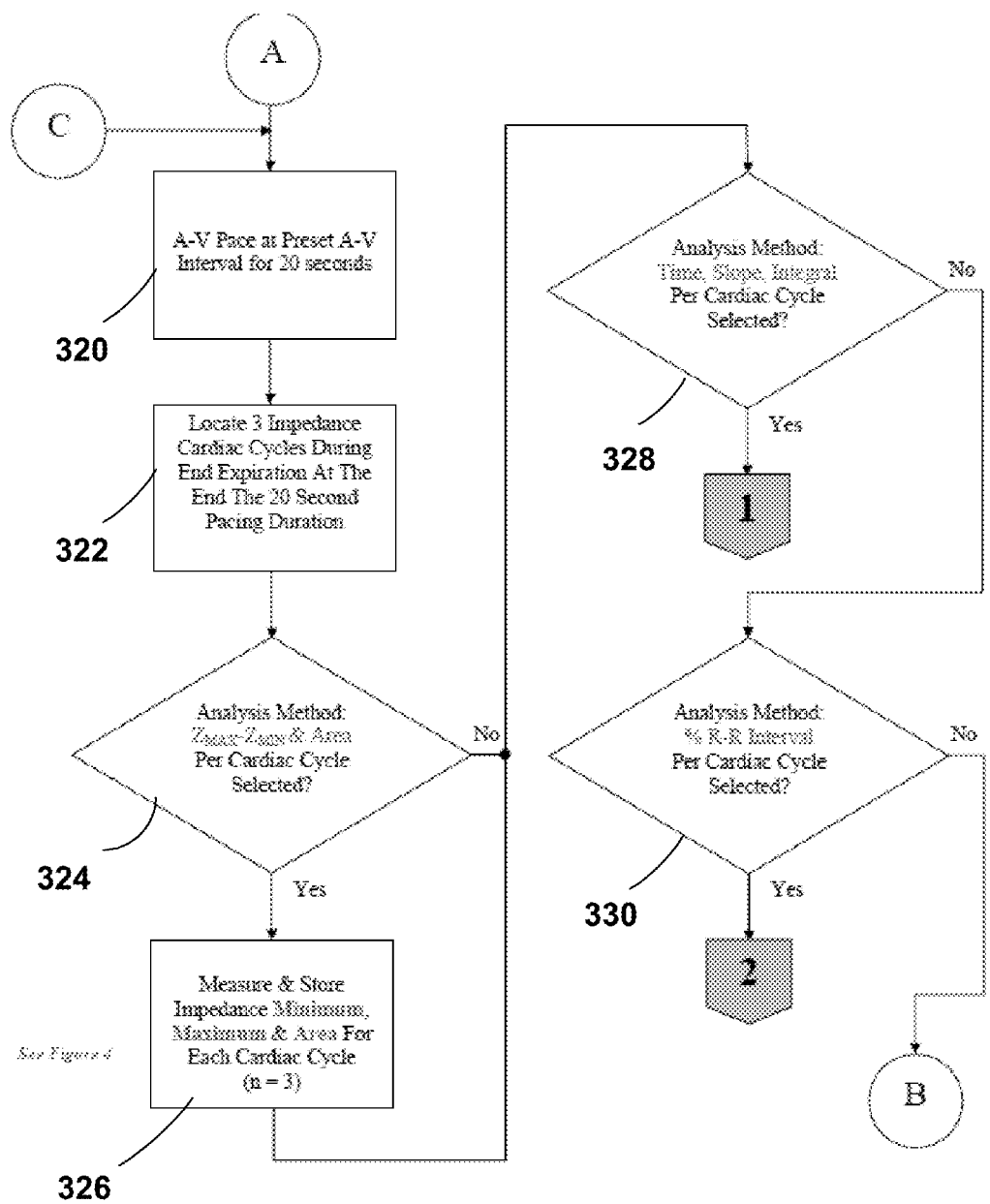

The process of acquiring selection data for the set AV interval (e.g., 20% of intrinsic conduction time), as shown in FIG. 16, may include AV pacing at the set or preset AV interval for a period of time (e.g., 20 seconds) (block 320). At the end of such time period, a plurality of cardiac cycles are located (block 322) (e.g., three cardiac cycles are located at the end of expiration in a respiratory cycle, such as, for example, described with reference to FIG. 6).

As shown by the decision block 324 in FIG. 16, if the measurement technique relating to the analysis of $Z_{MAX}$-$Z_{MIN}$ and Area per cardiac cycle is selected, then such parameters are measured and stored (block 326) (e.g., such measurements may be made as described with reference to FIG. 14) as selection data for use in analysis to determine the optimal AV delay. If such measurement technique was not selected, then it is determined whether the measurement technique relating to the analysis of Time, Slope, and Integral per cardiac cycle was selected (block 328).

Measurement and storage of such parameters, as well as others measured and stored per the algorithms described herein, is illustratively shown in FIGS. 23A-23C. Further, the storage of parameters derived from measured parameters is also illustrated therein (e.g., ratios calculated and stored as shown illustratively in FIG. 23C).

Figure 18:
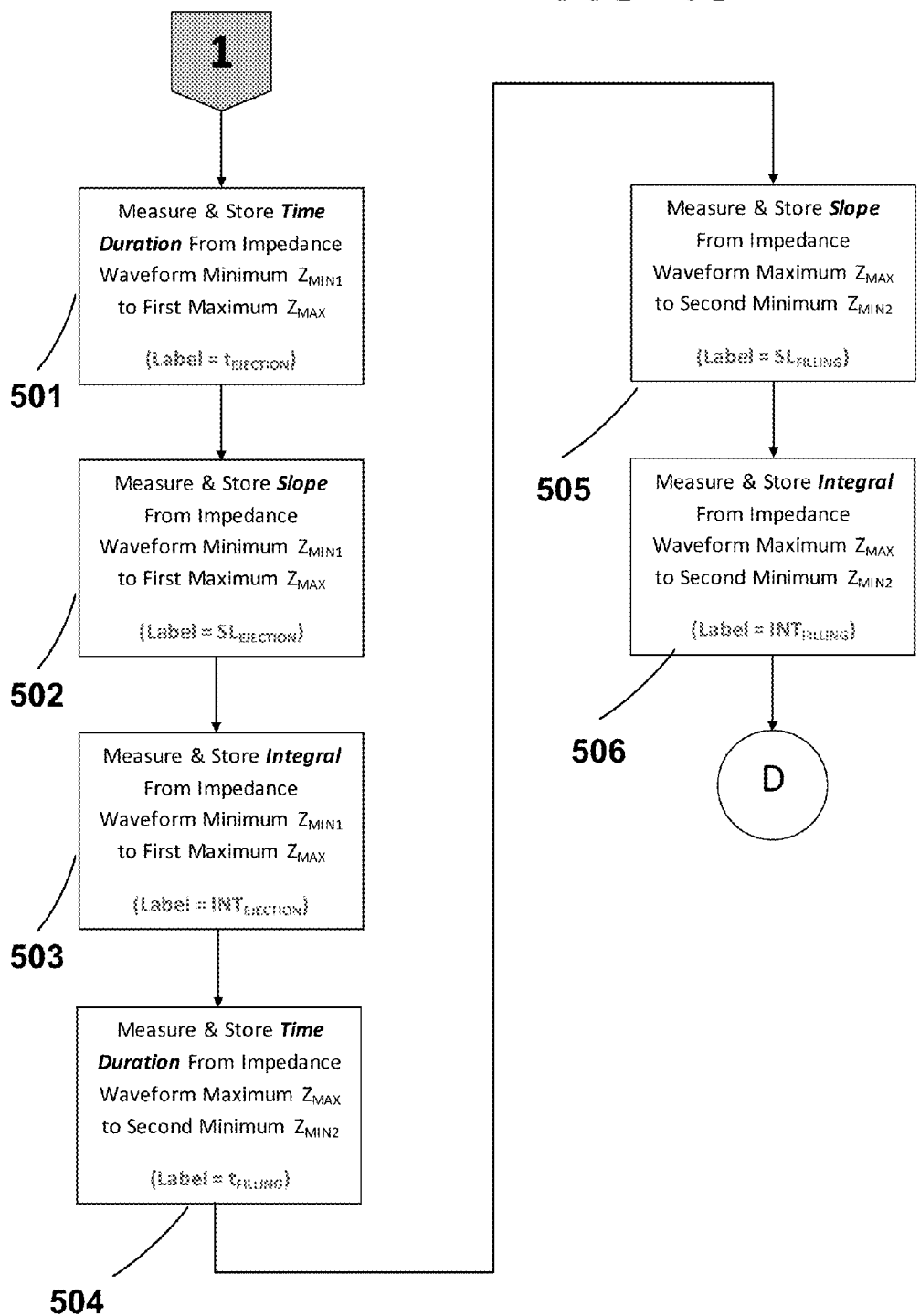

As shown by the decision block 328, if the measurement technique relating to the analysis of Time, Slope, and Integral per cardiac cycle was selected, then Subroutine 1 is performed. Subroutine 1 defines a method to measure the time duration, impedance waveform slope, and impedance waveform integral using the impedance waveform minimum to maximum period as the systolic portion of the cardiac cycle and the impedance waveform maximum to subsequent minimum of the following cardiac cycle as the diastolic portion of the cardiac cycle (see, for example, FIG. 11). For example, as shown in FIG. 18, Subroutine 1 may include performing and storing the following as shown in blocks 501-506: (block 501) Measure & Store Time Duration From Impedance Waveform Minimum $Z_{MIN1}$ to First Maximum $Z_{MAX}$ (Label=$t_{EJECTION}$); (block 502) Measure & Store Slope From Impedance Waveform Minimum $Z_{MIN1}$ to First Maximum $Z_{MA}$ (Label=$SL_{EJECTION}$); (block 503) Measure & Store Integral From Impedance Waveform Minimum $Z_{MIN1}$ to First Maximum $Z_{MAX}$ (Label=$INT_{EJECTION}$); (block 504) Measure & Store Time Duration From Impedance Waveform Maximum $Z_{MAX}$ to Second Minimum $Z_{MIN2}$ (Label=$t_{FILLING}$); (block 505) Measure & Store Slope From Impedance Waveform Maximum $Z_{MAX}$ to Second Minimum $Z_{MIN2}$ (Label=$SL_{FILLING}$); and (block 506) Measure & Store Integral From Impedance Waveform Maximum $Z_{MAX}$ to Second Minimum $Z_{MIN2}$ (Label=$INT_{FILLING}$).

Figure 19:
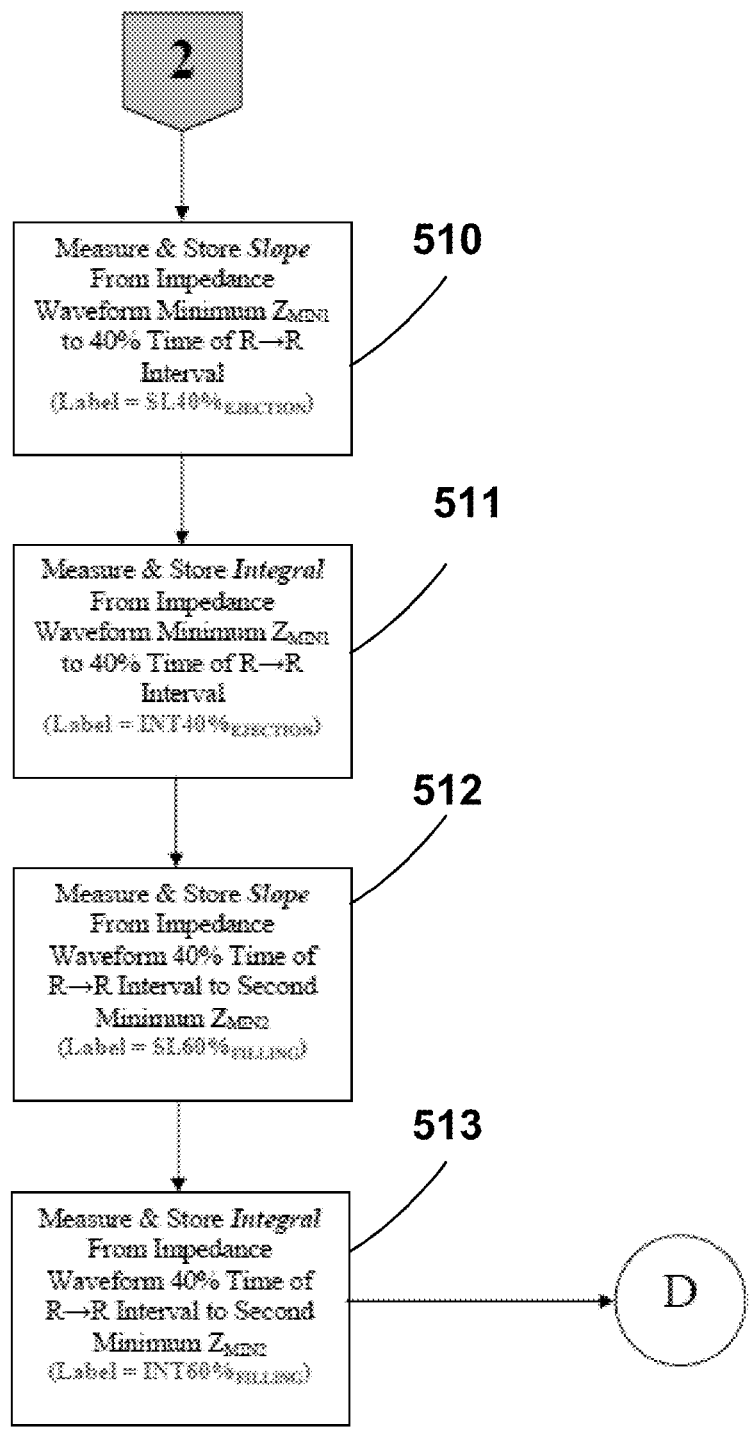

As shown by the decision block 328, if the measurement technique relating to the analysis of Time, Slope, and Integral per cardiac cycle was not selected, then it is determined whether the measurement technique relating to the analysis of a % of R-R Interval is determined (block 330). As shown by the decision block 330, if the measurement technique relating to the analysis of a % of R-R Interval was selected, then Subroutine 2 is performed. Subroutine 2 defines a method that may measure the impedance waveform slope and impedance waveform integral using 40% of the R-R interval as the defined period for the systolic portion of the cardiac cycle and the remaining 60% of the R-R interval as the diastolic portion of the cardiac cycle (see, for example, FIGS. 12 and 13). For example, as shown in FIG. 19, Subroutine 2 may include performing and storing the following as shown in blocks 510-513: (block 510) Measure & Store Slope From Impedance Waveform Minimum $Z_{MIN1}$ to 40% Time of R→R Interval (Label=$SL40\%_{EJECTION}$); (block 511) Measure & Store Integral From Impedance Waveform Minimum $Z_{MIN1}$ to 40% Time of R→R Interval (Label=$INT40\%_{EJECTION}$); (block 512) Measure & Store Slope From Impedance Waveform 40% Time of R→R Interval to Second Minimum $Z_{MIN2}$ (Label=$SL60\%_{FILLING}$); and (block 513) Measure & Store Integral From Impedance Waveform 40% Time of R→R Interval to Second Minimum $Z_{MIN2}$ (Label=$INT60\%_{FILLING}$).

Figure 20:
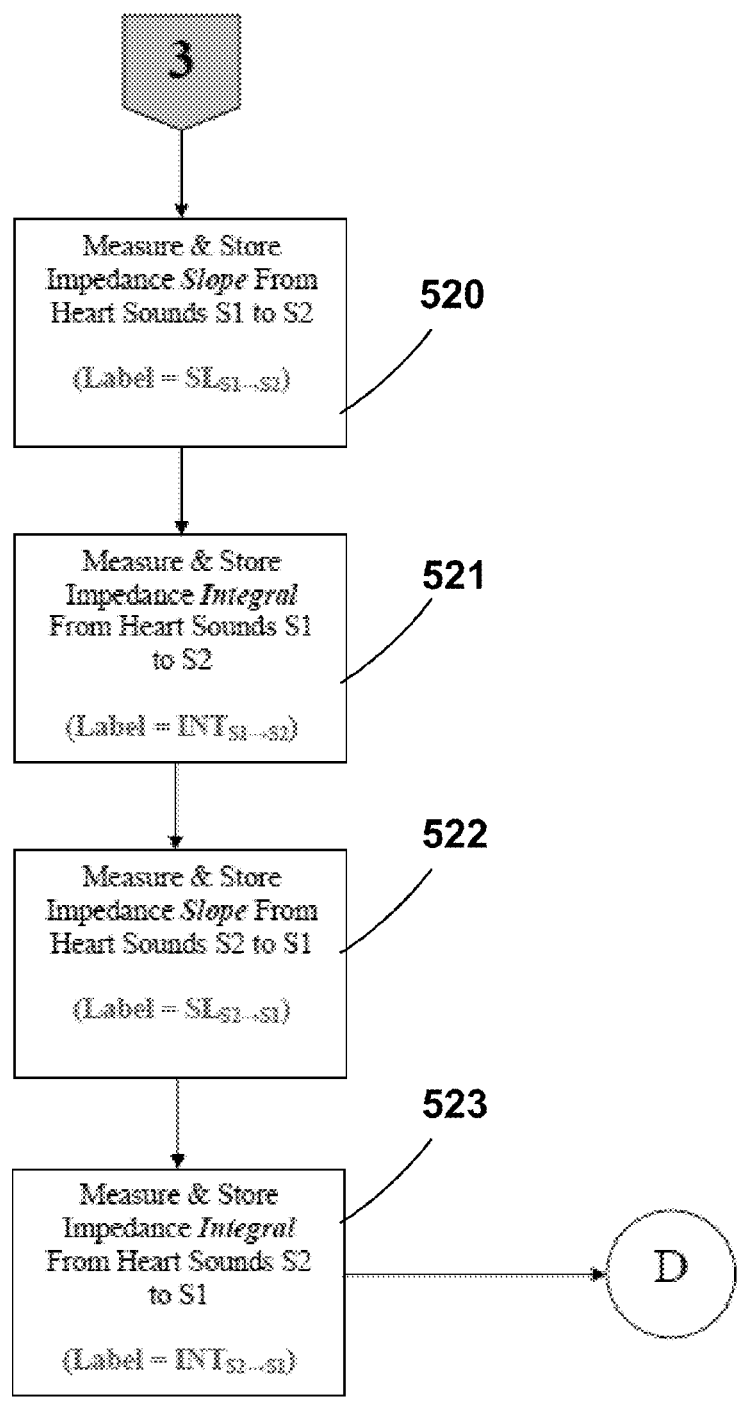

As shown by the decision block 330, if the measurement technique relating to the analysis of a % of R-R Interval was not selected, then it is determined whether the measurement technique relating to the analysis using heart sounds per cardiac cycle was selected (block 332). As shown by the decision block 332, if the measurement technique relating to the analysis using heart sounds was selected, then Subroutine 3 is performed. Subroutine 3 defines a method to measure the impedance waveform slope and impedance waveform integral using heart sounds S1 to S2 as the systolic portion of the cardiac cycle and heart sounds S2 to S1 of the following cardiac cycle as the diastolic portion of the cardiac cycle. For example, as shown in FIG. 20, Subroutine 3 may include performing and storing the following as shown in blocks 520-523: (block 520) Measure & Store Impedance Slope From Heart Sounds S1 to S2

(Label=$SL_{S1 \to S2}$); (block 521) Measure & Store Impedance Integral From Heart Sounds S1 to S2 (Label=$INT_{S1 \to S2}$); (block 522) Measure & Store Impedance Slope From Heart Sounds S2 to S1 (Label=$SL_{S2 \to S1}$); and (block 523) Measure & Store Impedance Integral From Heart Sounds S2 to S1 (Label=$INT_{S2-S1}$).

Figure 17:
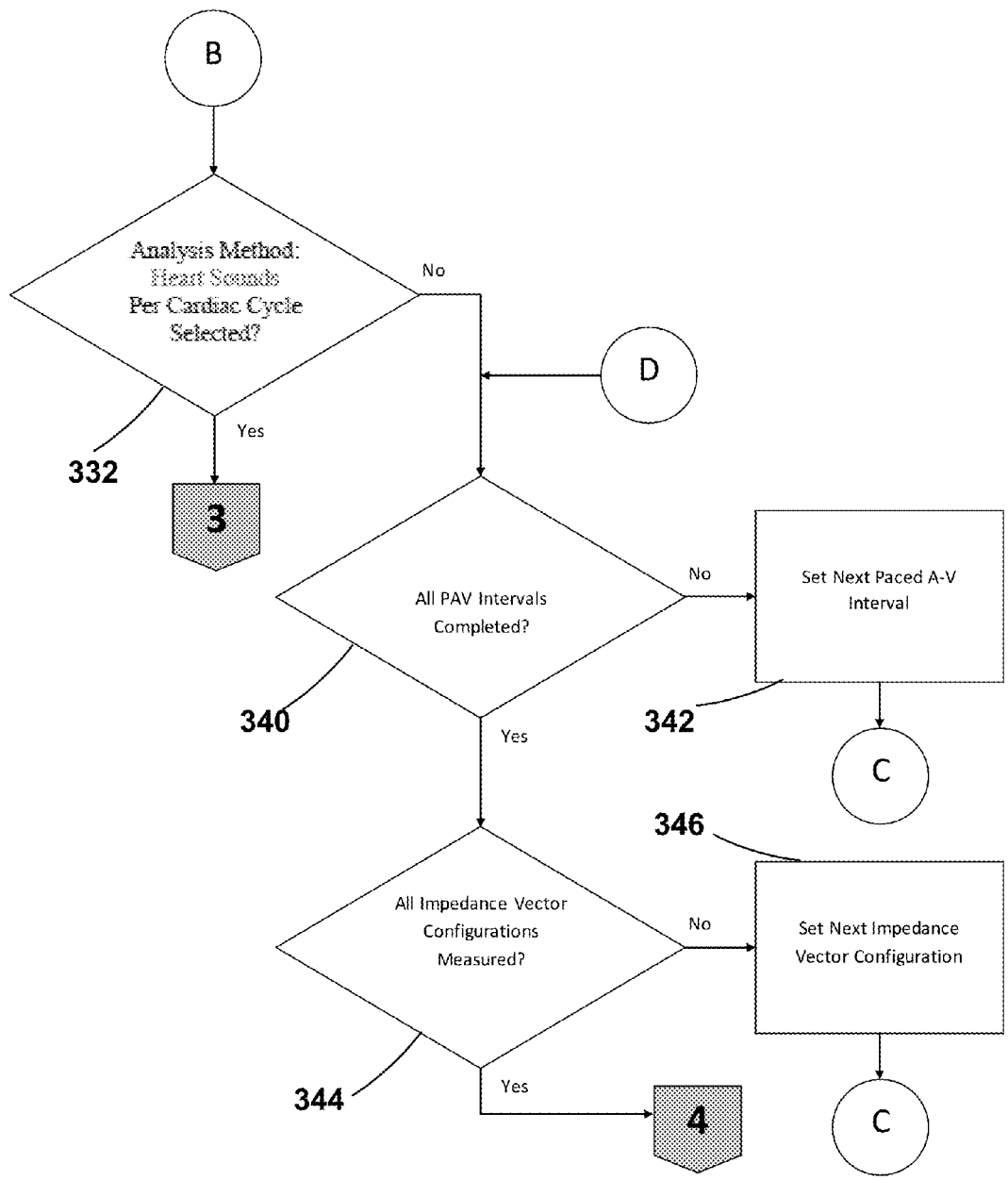

As shown by the decision block 332, if the measurement technique relating to the analysis using heart sounds was not selected, or if Subroutine 3 is completed, then as shown in FIG. 17, it is determined as illustrated in decision block 340 whether measurements have been acquired for all the AV interval options (e.g., 20% of intrinsic AV conduction, 30% of intrinsic AV conduction, etc.). If it is determined that measurements have not been acquired for all the AV interval options (e.g., 20% of intrinsic AV conduction, 30% of intrinsic AV conduction, etc.), then another AV interval option is set (block 342) and the measurement portion of the algorithm is repeated (e.g., Subroutines 1-3). Likewise, if measurements have not been acquired for all impedance vector configurations at each of the AV interval options (e.g., 20% of intrinsic AV conduction, 30% of intrinsic AV conduction, etc.) (block 344), then another or next impedance vector configuration is set (block 346) and the measurement portion of the algorithm is repeated (e.g., Subroutines 1-3). It will be recognized that, at least in one embodiment, optional AV intervals may be set and measurements may be collected at each of the impedance vector configurations, or, in at least one embodiment, each of the impedance vector configurations may be set and then the optional AV intervals are used for pacing to allow for acquisition of measurements. Whatever the order of making measurements, at least in one embodiment, measurements are made for each optional AV interval at each selected impedance vector configuration.

Figure 21:
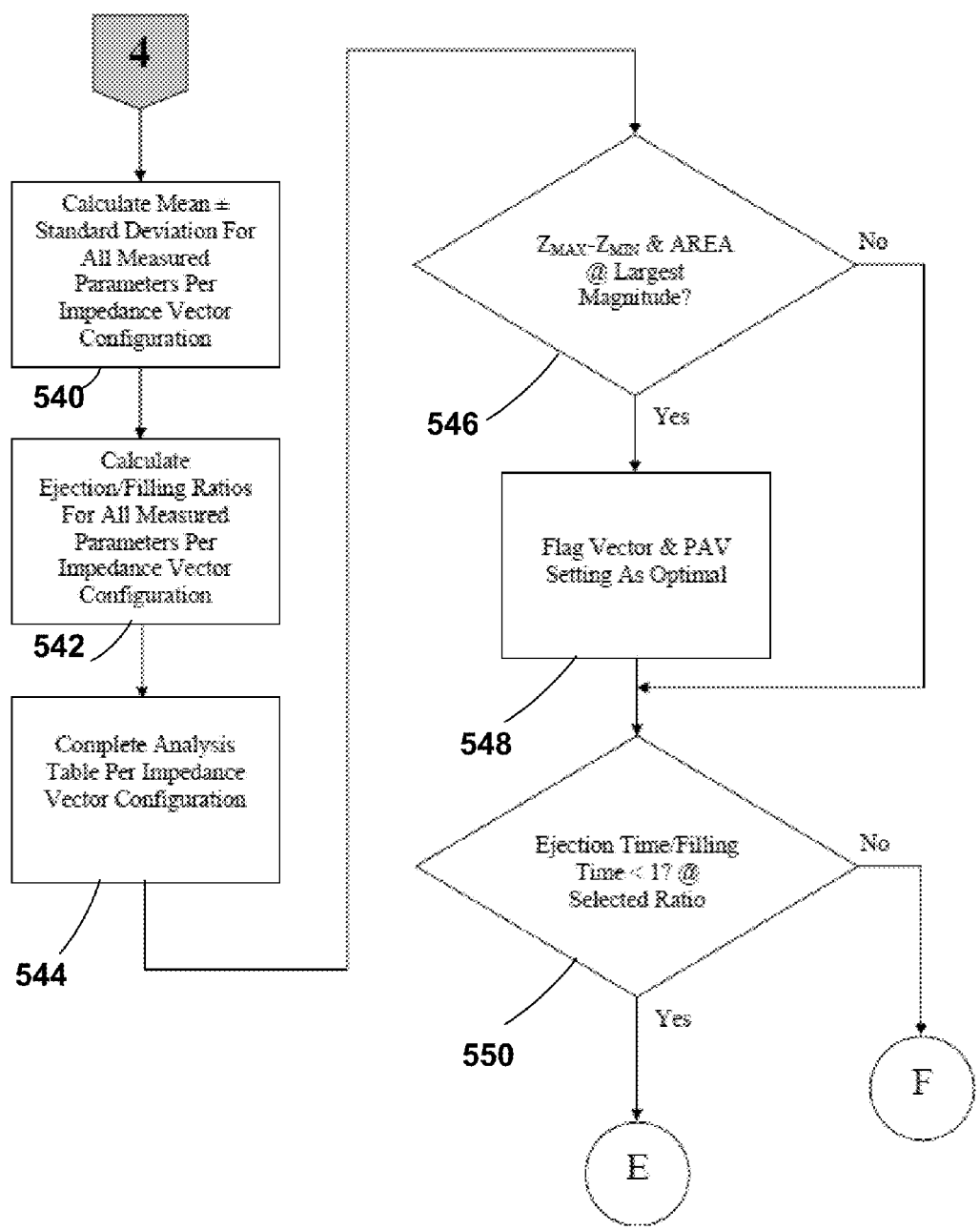
Figure 22:
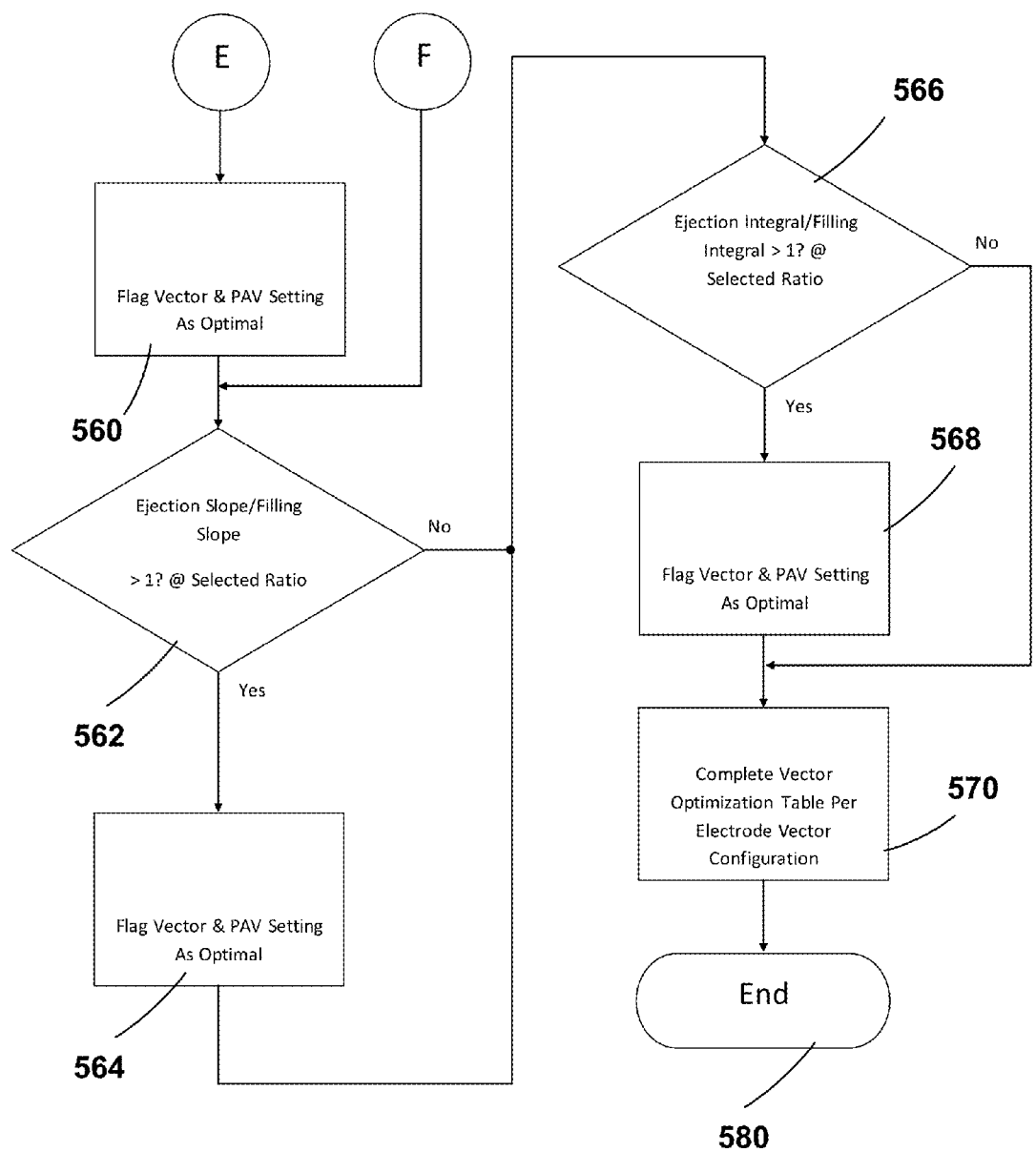

Following the completion of measurements at each impedance vector configuration for each of the plurality of optional AV intervals, Subroutine 4 as illustrated in FIGS. 21-22 may be carried out (e.g., more selection data may be determined, optimal AV delay setting may be selected, etc.). For example, Subroutine 4 defines a process to calculate and tabulate impedance waveform parameters per electrode vector configuration to determine optimal CRT therapy based on independent impedance values or ratios derived thereof. The Tables shown in FIGS. 23A-23C show measured impedance parameters, mean±standard deviation of all measured parameters calculated over a three cardiac cycle window and the ratios of the calculated parameters based on time, slope and integral values measured during the systolic and diastolic portions of the cardiac cycle. The Table shown in FIG. 24, a vector optimization table, determines which AV delay setting is optimal based on a scoring algorithm, e.g., the frequency of hits for each measured parameter.

For example, as shown in FIG. 21, the mean+/−standard deviation for all measured parameters per impedance vector configuration are calculated (block 540) and stored (e.g., as illustrated by FIGS. 23A-23B representative of memory storage, database configuration, etc.). Further, for example, ejection/filling ratios for all measured parameters per impedance vector configuration are calculated (block 542) and stored (e.g., as illustrated by FIG. 23C representative of memory storage, database configuration, etc.) and any further completion of analysis tables is carried out (block 544).

Following the completion of data gathering and storage, various types of analysis may be implemented to determine whether one of the plurality of AV delay options is to be set as the optimal AV delay for use in providing therapy. For example, as shown by decision block 546, if $Z_{MAX}-Z_{MIN}$ and AREA (e.g., as determined as described with reference to FIG. 14) are at the largest Magnitude, then the impedance vector configuration used to make such measurements is flagged and the paced AV interval for which such measurements were made is set as optimal (block 548). For example, at least in one embodiment, the AV delay is optimized after a vector configuration is selected. For example, with respect to AREA, one can calculate the sum of the AREA under each different AV delay setting for a vector configuration of a plurality of vector configurations, and then, use the summed AREA to select the vector configuration which gives the maximum summed AREA. If this is not the case, per decision block 546, the ratio of the ejection time versus filling time is analyzed per decision block 550.

For example, as shown by decision block 550, if Ejection Time/Filling Time (e.g., a ratio determined using the impedance measurements based on systolic and diastolic representative fiducial points) is less than one at a selected ratio, then the impedance vector configuration used to make such measurements is flagged and the paced AV interval for which such measurements were made is set as optimal (block 560). If this is not the case, the ratio of the ejection slope versus filling slope is analyzed per decision block 562.

For example, as shown by decision block 562, if Ejection Slope/Filling Slope (e.g., a ratio determined using the impedance measurements based on systolic and diastolic representative fiducial points) is less than one at a selected ratio, then the impedance vector configuration used to make such measurements is flagged and the paced AV interval for which such measurements were made is set as optimal (block 564). If this is not the case, per decision block 562, the ratio of the ejection integral versus filling integral is analyzed per decision block 566.

For example, as shown by decision block 566, if Ejection Integral/Filling Integral (e.g., a ratio determined using the impedance measurements based on systolic and diastolic representative fiducial points) is less than one at a selected ratio, then the impedance vector configuration used to make such measurements is flagged and the paced AV interval for which such measurements were made is set as optimal (block 568). If this is not the case, per decision block 566, then a vector optimization table per electrode vector configuration (e.g., such as shown in FIG. 24) is completed for further analysis.

For example, one illustrative vector optimization table for a particular vector shown in FIG. 24 includes a listing of various types of selection data in the left-hand column. Such data may be analyzed for each of the optional paced AV intervals (e.g., % of intrinsic AV conduction time), for example, by comparison to thresholds, comparison to one another, comparison from cycle to cycle, etc., to determine which of the optional AV intervals would be more effective than the corresponding to 60% of the intrinsic AV conduction time is indicated as scoring a hit, as shown for the Value of $SL_{EJECTION}$, the optional AV delay corresponding to 70% of the intrinsic AV conduction time is indicated as scoring a hit, etc. Further, as shown in FIG. 24, the most scored hits resulted for the paced AV delay corresponding to 70% of the intrinsic AV conduction time. As such, in this particular scoring embodiment, the paced AV delay corresponding to 70% of the intrinsic AV conduction time is set as the optimal AV delay for therapy.

Although the embodiment shown in FIG. 24 exemplifies that the optional AV delay selected as optimal is the AV delay having the most scored hits, it will be recognized that various scoring processes may be utilized (e.g., a weighted process may be used). For example, one or more of the scored hits for the AV delay corresponding to 60% of the intrinsic AV conduction time may be given different weight than those scored hits for the paced AV delay corresponding to 70% of the intrinsic AV conduction time; resulting in a higher weighted hit score for the AV delay corresponding to the 60% of intrinsic AV conduction as opposed to the 70% of intrinsic AV conduction time. In other words, such a weighted hit score would result in the selection of the paced AV delay corresponding to 60% of the intrinsic AV conduction time as opposed to 70%. Various weighting techniques may be used. For example, currently, in FIG. 24 no weight is applied (i.e., each hit is equally weighted by one (1)). For example, in FIG. 14, all the different parameters, such as, $Z_{MAX}$, $Z_{MIN}$, $Z_{MAX}-Z_{MIN}$, AREA, etc. has the same weight (e.g., which is one (1)). As such, in the Table of FIG. 24, 70% of Intrinsic AV has 15 hits since the weight for every parameter is 1, so the weighted hit is still 15, similarly 60% of intrinsic AV has weighted hit 7, and 50% of intrinsic AV has weighted hit 2. As such, the optimal setting is 70% of Intrinsic AV. However, in at least one embodiment, which may be more representative of reality, each parameter might perform differently in optimizing AV delay. Each parameter might be given different weights while calculating the final weighted hit. For instance, AREA might be given weight as 5, $INT_{EJECTION}$ might be given weight as 4, $t_{EJECTION}/t_{FILLING}$ might be given weight as 3, however, $Z_{MAX}$ might be given weight as 0.5, and $Z_{MIN}$ might be given weight as 0.5 as well, $SL_{FILLING}$ has a weight 2; this way, if the weighted hit is recalculated, one will get 14 weighted hit for 70% of intrinsic AV, 16 weighted hit for 60% of AV, 3 weighted hit for 50% of AV. As such, the optimal setting is rather 60% of intrinsic AV and not 70% of intrinsic AV.

In one or more embodiments, generally, impedance values of the electric path may define a periodic function, e.g., waveform, the period of which may be correlated with the cardiac cycle, or portions thereof and heart rate of the patient, in much the same manner that a cardiovascular pressure waveform defines a periodic function or portion contained within the periodic function. For example, the device implementing the processes described herein may compare an impedance, slope, area, integral or time duration of a first period to an impedance parameter of a subsequent period. The device may also compare a range (corresponding to the difference between the waveform maximum and the waveform minimum) of a first period to a range of a subsequent period. In any case, the device may determine whether the hemodynamic status of the patient has changed based on such comparisons between periods during the day, night, or circadian rhythms and optimize CRT based on input from all measurement time periods.

As described herein, successful implementation of CRT may require that the AV and VV delay be optimized. Optimizing AV and VV delay has been done with various sensing mechanisms such as EGM, arterial blood pressure, cutaneous impedance etc., and subsequently compared to the standard echocardiography optimization method. However, echocardiography optimization methods for CRT are often subjective and show high intra- and inter-individual variability. As such, one or more embodiments herein address this problem by measuring hemodynamic parameters with the implanted device using a single sensor to sense intracardiac impedance and another sensor to sense heart sound data. The heart sound data may be used to confirm a window time period for data to be extracted from an impedance signal based on the theory that the ejection period is primarily associated with the time between the impedance waveform minimum and maximum points, while the filling period is primarily associated with the impedance waveform maximum to a subsequent impedance minimum point on the following cardiac cycle. For example, dividing the impedance waveform into systolic and diastolic periods based on minimum and maximum points or time intervals between these points based on the % of the R-R interval, and then validating the measurement window by heart sounds S1 and S2, may be useful in defining systole and diastole. For example, FIG. 24 includes an exemplary table that shows that the optimal AV conduction time is chosen by the maximum number of parameter hits obtained for each intrinsic AV delay. Each parameter is calculated using the data extracted from the intracardiac impedance data and then a check mark is placed in the optimal intrinsic AV delay column. Additionally, each parameter can be accorded a different weight.

One or more of the following steps and/or features may be included in a medical device and/or an implantable medical device method: (a) acquiring heart sounds S1 and S2 from an electrode; (b) acquiring, about simultaneously with the heart sounds S1 and S2, an intracardiac impedance signal from a first electrode vector configuration; (c) extracting intracardiac impedance data between fiducial points on the intracardiac impedance signal; (d) associating each parameter with an optimal conduction time from a set of conduction times; (e) determining a maximum number of parameters are optimally associated with a conduction time from the set of conduction times; (f) assigning an effectiveness score to the first electrode vector configuration in response to step (e); (g) repeating steps (a)-(f) for a second electrode vector configuration; and (h) selecting one of the first and the second electrode vector configuration based upon their respective effectiveness score. For example, in one or more embodiments, the conduction time may be associated with one of an A-V delay and a V-V delay; the effectiveness score may be associated with one of an A-V delay and a V-V delay; the impedance fiducial points may include MVC and AVC, each of which are associated with impedance waveform minimum and maximum points, respectively; S1 and S2 may verify an ejection portion of a first cardiac cycle and a time interval for extracting impedance waveform measurements from the first and second intracardiac impedance signals; the impedance waveform maximum to a subsequent impedance waveform minimum and its associated subsequent heart sound S1 may determine the time interval for impedance waveform measurement for a diastolic period of the cardiac cycle while the impedance waveform minimum and its associated subsequent heart sound S2 may determine an end of a systolic portion of the cardiac cycle and a start of the diastolic filling portion of the cardiac cycle.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:
1. An implantable medical device for use in delivering cardiac resynchronization therapy to a patient's heart, wherein the cardiac resynchronization therapy is delivered based on a plurality of device parameters, the device comprising:

a sensing module configured to monitor at least an intracardiac impedance between at least two electrodes to provide an intracardiac impedance signal;

a therapy delivery module configured to deliver cardiac therapy to the patient's heart; and a control module coupled to the sensing module and the therapy delivery module and configured to:

deliver cardiac resynchronization therapy to a patient at a plurality of options for at least one of the device parameters;

acquire selection data relating to each of the plurality of options for the at least one device parameter for at least one cardiac cycle, wherein acquiring the selection data at each of the plurality of options of the device parameter comprises:

acquiring, at each of a plurality of electrode vector configurations, an intracardiac impedance signal, extracting a plurality of measurements from the intracardiac impedance signal for each of the plurality of electrode vector configurations, and determining selection data for each of the plurality of electrode vector configurations based on and corresponding to each of the plurality of extracted measurements from the intracardiac impedance signal;

provide a score for each of the plurality of options of the device parameter based on the acquired selection data determined based on and corresponding to each of the plurality of extracted measurements for each vector configuration; and select an option of the plurality of options of the device parameter based on the scores for the plurality of options of the device parameter for delivery of cardiac resynchronization therapy to the patient.

2. The device of claim 1, wherein to provide a score for each of the plurality of options of the device parameter based on the acquired selection data for each vector configuration comprises giving at least some of the selection data based on and corresponding to each of the plurality of extracted measurements from the intracardiac impedance signal different weight in determining a score than other selection data.

3. The device of claim 1, wherein the plurality of options of the device parameter comprises at least one of a plurality of paced A-V delays, a plurality of paced V-V delays, a plurality of pacing sites, and a plurality of locations for lead placement.

4. The device of claim 1, wherein the control module is further configured to use the acquired selection data to select an electrode vector configuration for delivery of cardiac resynchronization therapy to the patient.

5. The device of claim 4, wherein the control module is further configured to use the acquired selection data to set a delay selected from at least a plurality of paced A-V delays or at least a plurality of paced V-V delays for delivery of cardiac resynchronization therapy to the patient's heart using the selected electrode vector configuration.

6. The device of claim 1, wherein extracting the plurality of measurements from the intracardiac impedance signal comprises extracting one or more parameters comprising minimums, maximums, slopes, integrals, differentials, and timing at which one or more of such parameters occurs relative to one or more fiducial points associated with at least a part of a systolic portion of at least one cardiac cycle or at least part of a diastolic portion of the at least one cardiac cycle.

7. The device of claim 1, wherein the control module is configured to acquire temporal fiducial points associated with the systolic portion or a defined segment within the systolic portion of at least one cardiac cycle and temporal fiducial points associated with the diastolic portion or a defined segment within the diastolic portion of the at least one cardiac cycle for each of a plurality of electrode vector configurations, wherein the acquired temporal fiducial points are used for extracting the plurality of measurements from the intracardiac impedance signal.

8. The device of claim 7, wherein the temporal fiducial points associated with the systolic portion of at least one cardiac cycle and the temporal fiducial points associated with the diastolic portion of the at least one cardiac cycle comprise at least heart sounds representative of mitral valve closure (MVC) and aortic valve closure (AVC).

9. The device of claim 7, wherein the temporal fiducial points associated with the systolic portion of at least one cardiac cycle and the temporal fiducial points associated with the diastolic portion of the at least one cardiac cycle comprise temporal fiducial points defined by at least intracardiac impedance signal minimum and maximum points, and further wherein acquiring the selection data comprises extracting the plurality of measurements from the intracardiac impedance signal for each of the plurality of electrode vector configurations based at least in part on the temporal fiducial points defined by the intra-cardiac impedance signal minimum point and maximum point.

10. An implantable medical device method for delivering cardiac resynchronization therapy to a patient's heart, wherein the cardiac resynchronization therapy is delivered based on a plurality of device parameters, the method comprising:

delivering cardiac resynchronization therapy to a patient at a plurality of options for at least one of the device parameters;

acquiring selection data relating to each of the plurality of options for the at least one device parameter for at least one cardiac cycle, wherein acquiring the selection data at each of the plurality of options of the device parameter comprises:

acquiring, at each of a plurality of electrode vector configurations, an intracardiac impedance signal, extracting a plurality of measurements from the intracardiac impedance signal for each of the plurality of electrode vector configurations, and determining selection data for each of the plurality of electrode vector configurations based on and corresponding to each of the plurality of extracted measurements from the intracardiac impedance signal;

providing a score for each of the plurality of options of the device parameter based on the acquired selection data determined based on and corresponding to each of the plurality of extracted measurements for each vector configuration; and selecting an option of the plurality of options of the device parameter based on the scores for the plurality of options of the device parameter for delivery of cardiac resynchronization therapy to the patient.

11. The method of claim 10, wherein providing a score for each of the plurality of options of the device parameter based on the acquired selection data for each vector configuration comprises giving at least some of the selection data based on and corresponding to each of the plurality of extracted measurements from the intracardiac impedance signal different weight in determining a score than other selection data.

12. The method of claim 10, wherein the plurality of options of the device parameter comprises at least one of a plurality of paced A-V delays, a plurality of paced V-V delays, a plurality of pacing sites, and a plurality of locations for lead placement.

13. The method of claim 10, wherein method further comprises using the acquired selection data to select an electrode vector configuration for delivery of cardiac resynchronization therapy to the patient.

14. The method of claim 13, wherein selecting an option of the plurality of options of the device parameter based on the scores for the plurality of options of the device parameter for delivery of cardiac resynchronization therapy to the patient comprises using the acquired selection data to set a delay of at least a plurality of paced A-V delays or at least a plurality of paced V-V delays for delivery of cardiac resynchronization therapy to the patient's heart using the selected electrode vector configuration.

15. The method of claim 10, wherein extracting a plurality of measurements from the intracardiac impedance signal comprises extracting one or more parameters comprising minimums, maximums, slopes, integrals, differentials, and timing at which one or more of such parameters occurs relative to one or more fiducial points associated with at least a part of a systolic portion of at least one cardiac cycle or at least a part of a diastolic portion of the at least one cardiac cycle.

16. The method of claim 10, wherein the method further comprises acquiring temporal fiducial points associated with the systolic portion or a defined segment within the systolic portion of at least one cardiac cycle and temporal fiducial points associated with the diastolic portion or a defined segment within the diastolic portion of the at least one cardiac cycle for each of a plurality of electrode vector configurations, wherein the acquired temporal fiducial points are used for extracting the plurality of measurements from the intracardiac impedance signal.

17. The method of claim 16, wherein the temporal fiducial points associated with the systolic portion of at least one cardiac cycle and the temporal fiducial points associated with the diastolic portion of the at least one cardiac cycle comprise at least heart sounds representative of mitral valve closure (MVC) and aortic valve closure (AVC).

18. The method of claim 16, wherein the temporal fiducial points associated with the systolic portion of at least one cardiac cycle and the temporal fiducial points associated with the diastolic portion of the at least one cardiac cycle comprise temporal fiducial points defined by at least intra-cardiac impedance signal minimum and maximum points, and further wherein the acquiring the selection data comprises extracting the plurality of measurements from the intracardiac impedance signal for each of the plurality of electrode vector configurations based at least in part on the temporal fiducial points defined by the intra-cardiac impedance signal minimum point and maximum point.

19. The method of claim 16, wherein the temporal fiducial points associated with the systolic portion of at least one cardiac cycle comprise at least points associated with a first predetermined portion of an R-R interval and the temporal fiducial points associated with the diastolic portion of the at least one cardiac cycle comprise at least points associated with a second predetermined portion of the R-R interval, and further wherein acquiring selection data comprises extracting the plurality of measurements from the intracardiac impedance signal for each of the plurality of electrode vector configurations based at least in part on temporal fiducial points associated with a first predetermined portion of an R-R interval and based at least in part on temporal fiducial points associated with a second predetermined portion of an R-R interval.

* * * * *